(12) United States Patent
Lazo Vázquez et al.

(10) Patent No.: US 7,790,173 B2
(45) Date of Patent: Sep. 7, 2010

(54) PHARMACEUTICAL COMPOUND CAPABLE OF INDUCE IMMUNE PROTECTIVE RESPONSE AGAINST DENGUE VIRUS HAVING THE CAPSID PROTEIN OF THE DENGUE VIRUS

(75) Inventors: Laura Lazo Vázquez, Ciudad de la Habana (CU); Lisset Hermida Cruz, Ciudad de la Habana (CU); Carlos López Abarrategui, Ciudad de la Habana (CU); Beatriz de la Caridad Sierra Vázquez, Ciudad de la Habana (CU); Susana Vázquez Ramundo, Ciudad de la Habana (CU); Iris Valdez Prado, Ciudad de la Habana (CU); Gerardo Enrique Guillen Nieto, Ciudad de la Habana (CU); Maria Guadalupe Guzmán Tirado, Ciudad de la Habana (CU); Aida Zulueta Morales, Ciudad de la Habana (CU)

(73) Assignee: Centro de Ingenieria Genetica Y Biotecnologia, Cuidad de la Habana (CU)

( * ) Notice: Subject to any disclaimer, the term of this patent is extended or adjusted under 35 U.S.C. 154(b) by 0 days.

(21) Appl. No.: 12/067,129

(22) PCT Filed: Sep. 18, 2006

(86) PCT No.: PCT/CU2006/000008
§ 371 (c)(1),
(2), (4) Date: Jul. 23, 2008

(87) PCT Pub. No.: WO2007/031034
PCT Pub. Date: Mar. 22, 2007

(65) Prior Publication Data
US 2008/0311157 A1  Dec. 18, 2008

(30) Foreign Application Priority Data
Sep. 16, 2005 (CU) .......................... CU2005-0168

(51) Int. Cl.
A61K 39/00 (2006.01)
A61K 39/12 (2006.01)
(52) U.S. Cl. ............... 424/192.1; 424/202.1; 424/218.1
(58) Field of Classification Search ................ None
See application file for complete search history.

(56) References Cited

U.S. PATENT DOCUMENTS 7,279,164 B2   10/2007  Cruz et al.
2004/0259224 A1*  12/2004  Guirakhoo ............... 435/235.1

FOREIGN PATENT DOCUMENTS

EP           0474313  A2    3/1992
EP           1418180  A2    5/2004
EP           1454988  A1    9/2004
WO           WO9306214  A1   4/1993
WO           WO 96/37221  A1  11/1996
WO           WO 97/26359  A1  7/1997
WO           WO9743310  A1   11/1997
WO           WO9823754  A1   6/1998
WO           WO 9831814  A1   7/1998
WO           WO9907733  A2   2/1999
WO           WO9918216  A2   4/1999
WO           WO 00/66791  A1  11/2000
WO           WO 02/95075  A1 *  5/2002
WO           WO2004052293  A2   6/2004
WO           WO2005002501  A2   1/2005
WO           WO2006078657  A2   7/2006
WO           WO2006136697  A2   12/2006
WO           WO2007124698  A2   11/2007

OTHER PUBLICATIONS

Mustafa et al. MJAFI, 2008, 64:161-164.*
Monath et al. NEJM 2007, 357(22):2222-2225.*
Shresta et al., Journal of Virology, 2006, 80(20):10208-10217.*
Database UniPrto (online) Subname: Full=Polyprotein; XP002492705 retrieved from EBI accession No. UNIPROT: Q2QFY7 Database accession No. Q2QFY7 the whole document (Jan. 24, 2006).
Portal-Nunez S. et al., "Peptide Inhibitors of Hepatitis C Virus NS3 Protease" Antiviral Chemistry & Chemotherapy, Blackwell Scientific Publ. London, GB, vol. 14, No. 5, 225-233 (2003).
Lanciotti, Robert S., et al., "Molecular evolution and phylogeny of dengue-4 viruses", Journal of General Virology 1997, 78(9):2279-2286.
Chaturvedi et al., "Dengue Vaccines: Problems and Prospects," Indian J. Med. Res. vol. 121, May 2005, pp. 639-652.
Goncalvez et al., "Epitope Determinants of a Chimpanzee Fab Antibody that Efficiently Cross-Neutralizes Dengue Type 1 and Type 2 Viruses Map to Inside and in Close Proximity to Fusion Loop of the Dengue Type 2 Virus Envelope Glycoprotein", Journal of Virology, 78(23):12919-12928(2004).
Zulueta, et al. "The Fusion Site of Envelope Fragments from Each Serotype of Dengue Virus in the P64k Protein, Influence Some Parameters of the Resulting Chimeric Constructs", Biochemical and Biophysical Research Communications, 308, 619-626 (2003).
Lazo et al., "A Recombinant Capsid Protein from Dengue-2 Induces Protection in Mice Against Homologous Virus", Vaccine 25, 1064-1070 (2007).
Irie et al., "Sequence analysis of cloned dengue virus type 2 genome (New Guinea-C strain)", Department of Biochemistry and Molecular Biology, University of Kansas Medical Center, Gene 75 197-211 (1989).
Zhao et al., "Cloning Full-Length Dengue Type 4 Viral DNA Sequences: Analysis of Genes Coding for Structrual Proteins", Virol. 155:77-88 (1986).

(Continued)

*Primary Examiner*—Stacy B Chen
(74) *Attorney, Agent, or Firm*—Hoffmann & Baron, LLP

(57) ABSTRACT

This invention describes a pharmaceutical compound which has the capsid protein of Dengue virus and which is capable of inducing, in the receptor, a protective immune response before the viral challenge, without inducing the Ab-dependent enhancement phenomenon.

10 Claims, 4 Drawing Sheets

OTHER PUBLICATIONS

Figure 5:
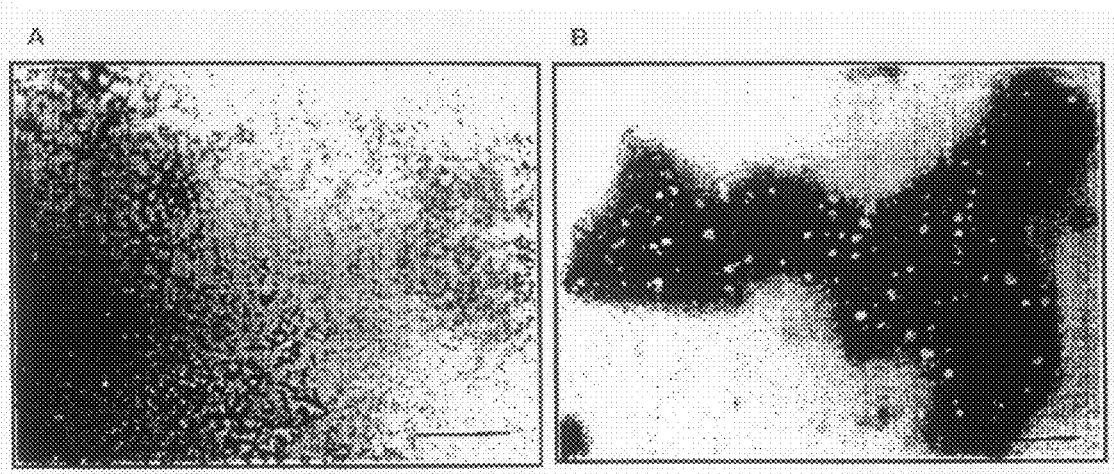
Figure 6:
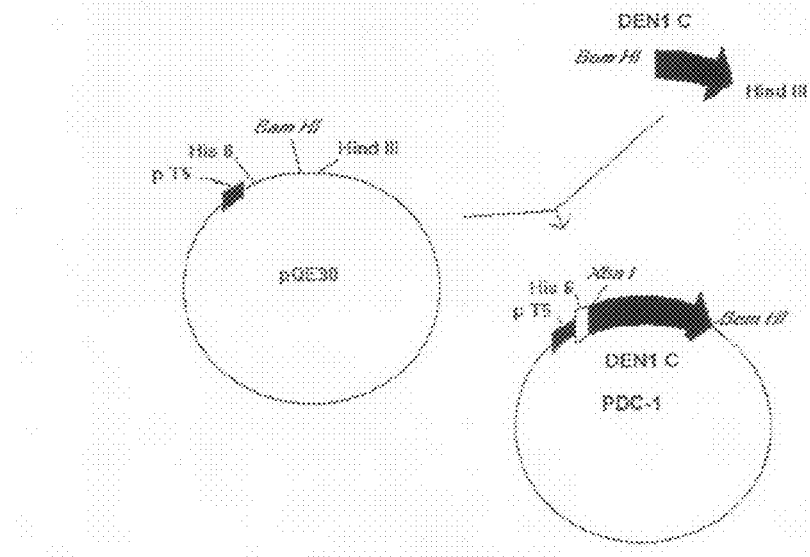

Shiryaev Sergey A et al., "Cleavage Targets and the D-Arginine-Based Inhibitors of the West Nile Virus NS3 Processing Proteinase", Biochemical Journal, vol. 393, No. Part 2, 503-511 (2006).

Deshayes S. et al., "Cell-Penetrating Peptides: Tools for Intracellular Delivery of Therapeutics", CMLS Cellular and Molecular Live Sciences, Birkhauser-Verlag, BA, vol. 62, No. 16, 1839-1849 (2005).

Blok, J., et al., "Variation of the Nucleotide and Encoded Amino Acid Sequences of the Envelope Gene from Eight Dengue-2 Viruses", Archives of Virology 1989, 105(1-2):39-53.

Lanciotti, Robert S., et al., "Molecular evolution and epidemiology of dengue-3 viruses", Journal of General Virology 1994, 75(1):65-75.

Silva, Ricardo, et al., "Characterisation of the 1pdA gene from Neisseria meningitidis by polymerase chain reaction, restriction fragment length polymorphism and sequencing", FEMS Microbiology Letters May 1999, 174 (1):191-199.

Tettelin, Nerve, et al., "Complete Genome Sequence of Neisseria meningitidis Serogroup B Strain MC58", Science 2000, 287(5459):1809-1815.

Wang, Eryu, et al., "Evolutionary Relationships of Endemic/Epidemic and Sylvatic Dengue Viruses", Journal of Virology 2000, 74(7):3227-3234.

Perez et al., "Safety and Preliminary Immunogenicity of the Recombinant Outer Membrane Protein P64K of Neiseria Meningitis in Human Volunteers," Biotechnol. Appl. Biochem, 34, 121-125 (2001).

Pugachev et al., "New Developments in Flavivirus Vaccines with Special Attention to Yellow Fever," Curr Opin Infect Dis 18:387-394 (2005).

Murray, et al., "Processing of the Dengue Virus Type 2 Proteins prM and C-prM", Journal of General Virology, 74, 175-182 (1993).

Srivastava et al., "Mice Immunized with a Dengue Type 2 Virus E and NS1 Fusion Protein Made in Escherichia coli are Protected Against Lethal Dengue Virus Infection," Vaccine vol. 13, No. 13 (1995).

Mason et al., "The Antigenic Structure of Dengue Type I Virus Envelope with NS1 Proteins Expressed in Escherichia Coli", Journal of General Virology, 71, 2107-2114(1990).

Mota et al., "Induction of Protective Antibodies Against Dengue Virus by Tetravalent DNA Immunization of Mice with Domain III of the Envelope Protein", Vaccine 23, 3469-3476(2005).

Database EBI (Online) Envelope Glycoprotein (Fragment) Shu L. and Zuo, L. "No Title" XP002430600 Retrieved from UNIPROT/TREMBL accession No. Q7TLC5, Database accession No. Q7TLC5 - Abstract. (2008).

Thullier et al., "A recombinant Fab Neutralizes Dengue Virus in Vitro", Journal of Biotechnology, Elsevier Science Publishers, vol. 69, No. 2-3, pp. 183-190 (1999) Abstract.

Randolph et al., "Acidotropic Amines Inhibit Proteolytic Processing of Flavivirus prM Protein", Virology 174, 450-458 (1990).

Gruenberg et al., "Partial Nucleotide Sequence and Deduced Amino Sequence of the Structural Proteins of Dengue Virus Type 2, New Guinea C and PUO-218 Strains", J. gen Virol. 69, 1391-1398 (1988).

Gaines et al., "Pathogen-Derived Resistance to Dengue Type 2 Virus in Mosquito Cells by Expression of the Premembrane Coding Region of the Viral Genome", Journal of Virology, p. 2132-2137 (1996).

Kaufman et al., "Monoclonal Antibodies for Dengue Virus PRM Glycoprotein Protect Mice Against Lethal Dengue Infection", Am. J. Trop. Med. Hyg., 41(5), pp. 576-580 (89-157) 1989.

Bray et al., "Dengue Virus Premembrane and Membrane Proteins Elicit a Protection Immune Response", Virology, 185, 505-508 (1991).

* cited by examiner

Figura 1.
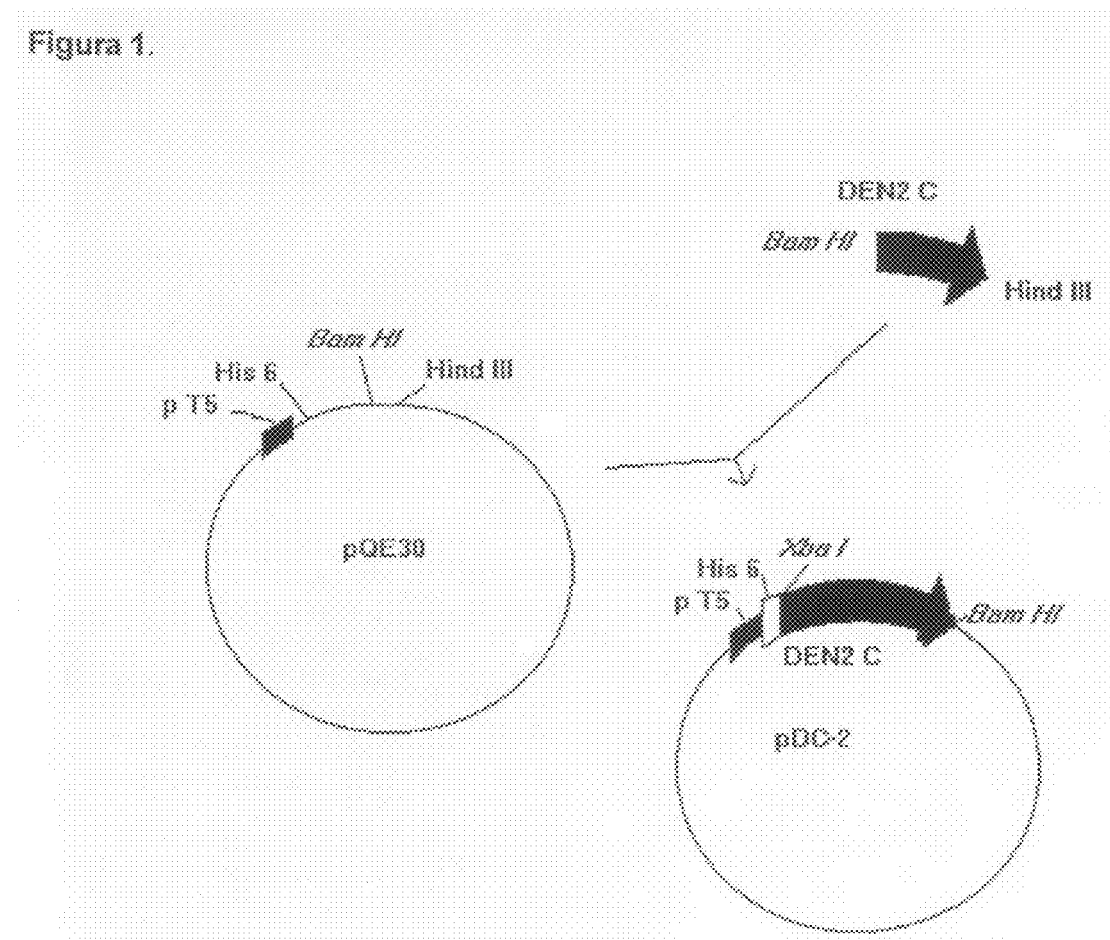
Figura 2.
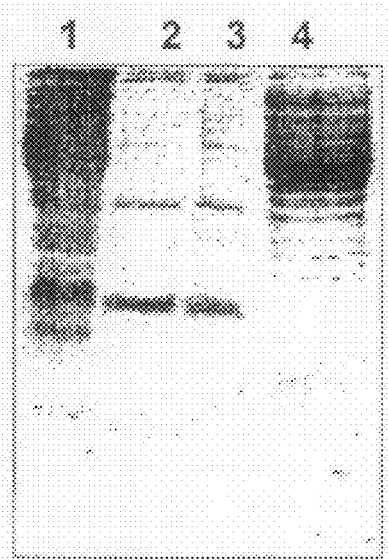

Figura 3.
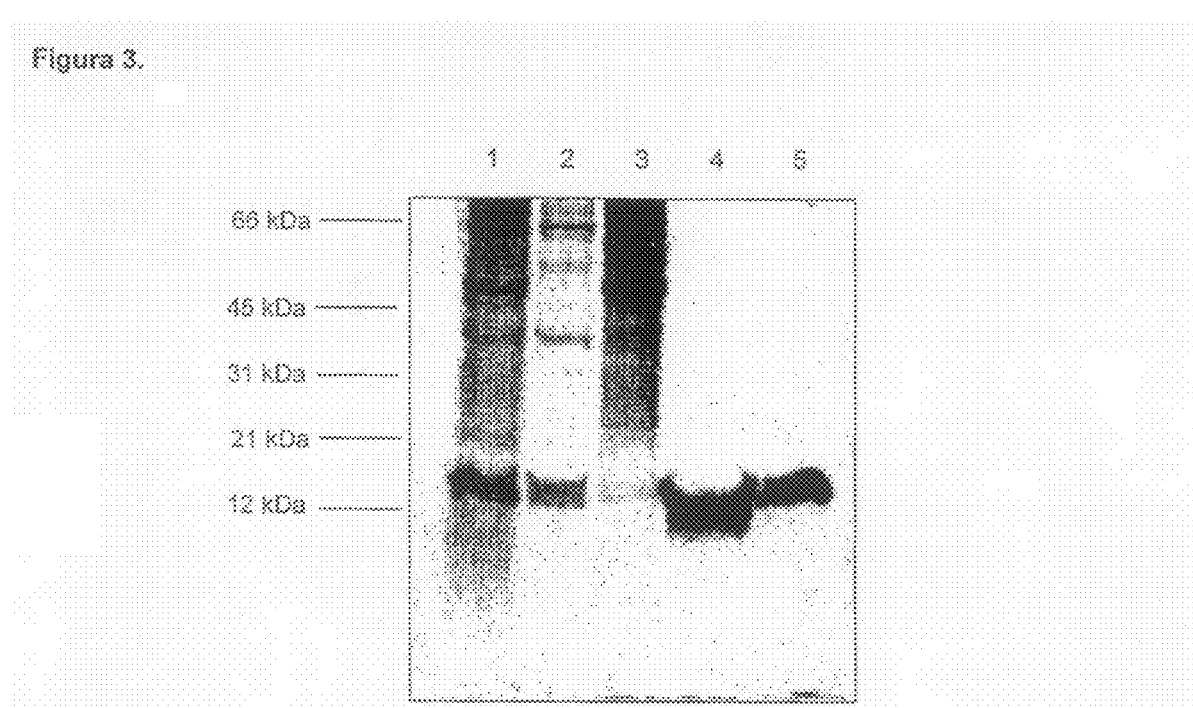
Figura 4.
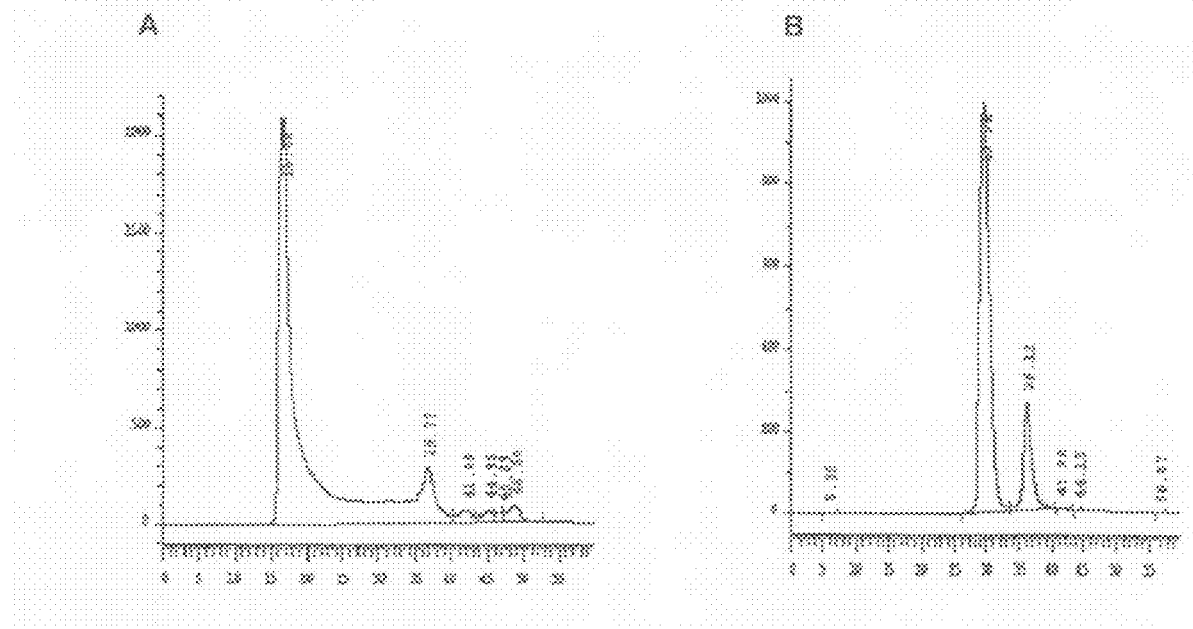

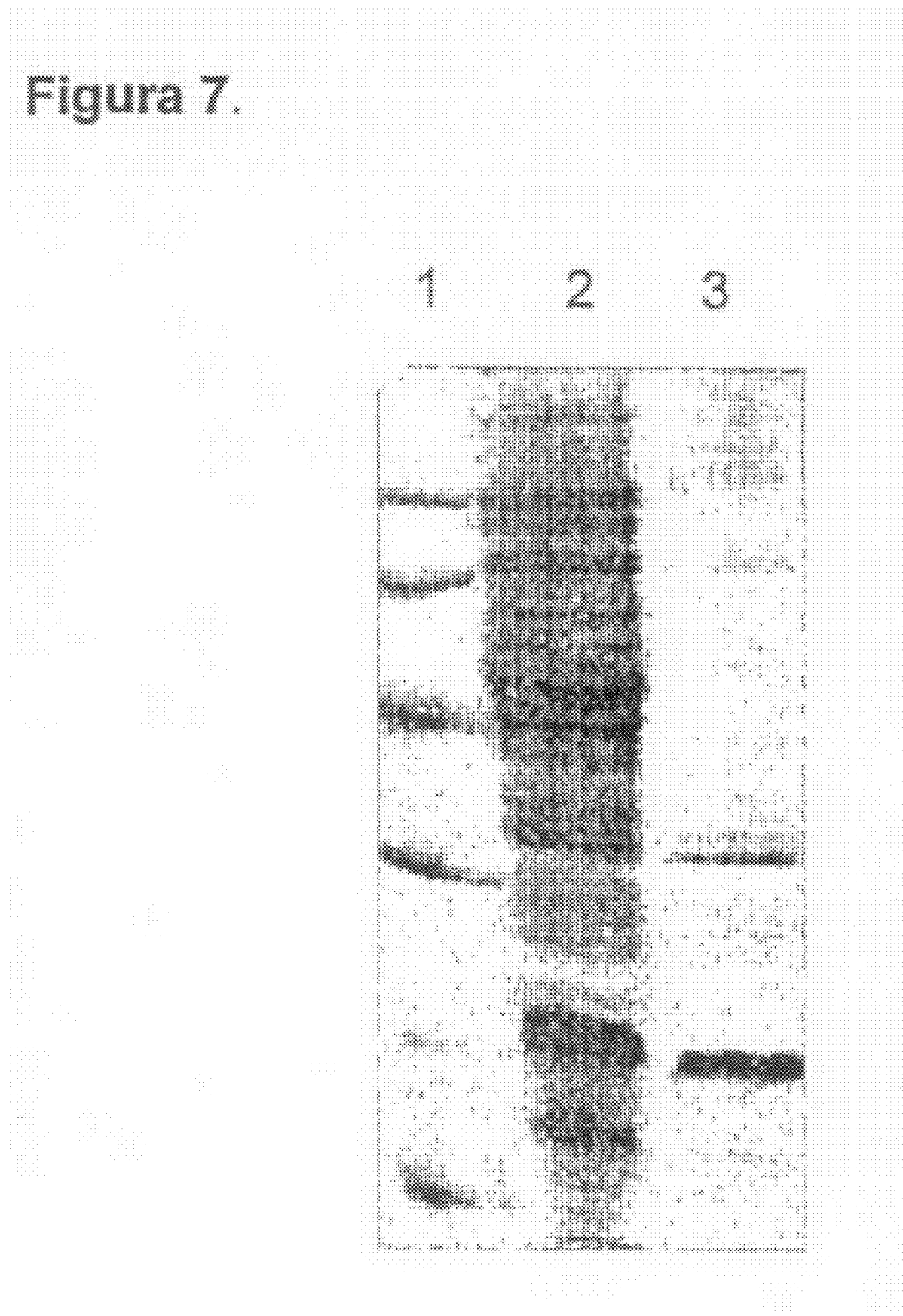
Figura 7.

SEQUENCE LISTING

<160> NUMBER OF SEQ ID NOS: 24

<210> SEQ ID NO 1
<211> LENGTH: 24

```
<212> TYPE: DNA
<213> ORGANISM: Dengue virus

<400> SEQUENCE: 1
cgggatccaa taaccaacga aaaa                                              24

<210> SEQ ID NO 2
<211> LENGTH: 23
<212> TYPE: DNA
<213> ORGANISM: Dengue Virus

<400> SEQUENCE: 2
acaagctttt acctgcgtct cct                                               23

<210> SEQ ID NO 3
<211> LENGTH: 339
<212> TYPE: DNA
<213> ORGANISM: Dengue virus

<400> SEQUENCE: 3
aataaccaac gaaaaaaggc gagaagtacg cctttcaata tgctgaaacg cgagagaaac        60
cgcgtgtcaa ctgtgcaaca gctgacaaag agattctcac ttggaatgct gcaaggacga      120
ggaccattaa aactgttcat ggcccttgtg gcgttccttc gtttcctaac aatcccacca      180
acagcaggga tactgaaaag atggggaacg atcaaaaaat caaaagctat caatgttttg      240
agagggttca ggaaagagat tggaaggatg ctgaacatct tgaacaggag acgcaggaca      300
gcaggcgtga ttattatgtt gattccaaca gcgatggcg                             339

<210> SEQ ID NO 4
<211> LENGTH: 339
<212> TYPE: DNA
<213> ORGANISM: Dengue virus

<400> SEQUENCE: 4
atgagaggat cgcatcacca tcaccatcac ggatccaata accaacgaaa aaaggcgaga       60
agtacgcctt tcaatatgct gaaacgcgag agaaaccgcg tgtcaactgt gcaacagctg      120
acaaagagat tctcacttgg aatgctgcaa ggacgaggac cattaaaact gttcatggcc      180
cttgtggcgt tccttcgttt cctaacaatc ccaccaacag cagggatact gaaaagatgg      240
ggaacgatca aaaaatcaaa agctatcaat gttttgagag ggttcaggaa agagattgga      300
aggatgctga acatcttgaa caggagacgc aaaagctt                              339

<210> SEQ ID NO 5
<211> LENGTH: 111
<212> TYPE: PRT
<213> ORGANISM: Dengue virus

<400> SEQUENCE: 5

Met Arg Gly Ser His His His His His His Gly Ser Asn Asn Gln Arg
1               5                   10                  15

Lys Lys Ala Arg Ser Thr Pro Phe Asn Met Leu Lys Arg Glu Arg Asn
            20                  25                  30

Arg Val Ser Thr Val Gln Gln Leu Thr Lys Arg Phe Ser Leu Gly Met
        35                  40                  45

Leu Gln Gly Arg Gly Pro Leu Lys Leu Phe Met Ala Leu Val Ala Phe
    50                  55                  60

Leu Arg Phe Leu Thr Ile Pro Pro Thr Ala Gly Ile Leu Lys Arg Trp
65                  70                  75                  80
```

```
Gly Thr Ile Lys Lys Ser Lys Ala Ile Asn Val Leu Arg Gly Phe Arg
            85                  90                  95

Lys Glu Ile Gly Arg Met Leu Asn Ile Leu Asn Arg Arg Arg Arg
            100                 105                 110

<210> SEQ ID NO 6
<211> LENGTH: 3461
<212> TYPE: DNA
<213> ORGANISM: Artificial Sequence
<220> FEATURE:
<223> OTHER INFORMATION: plasmid pQE-30

<400> SEQUENCE: 6
ctcgagaaat cataaaaaat ttatttgctt tgtgagcgga taacaattat aatagattca      60
attgtgagcg ataacaatt tcacacagaa ttcattaaag aggagaaatt aactatgaga     120
ggatcgcatc accatcacca tcacggatcc gcatgcgagc tcggtacccc gggtcgacct     180
gcagccaagc ttaattagct gagcttggac tcctgttgat agatccagta atgacctcag     240
aactccatct ggatttgttc agaacgctcg gttgccgccg ggcgtttttt attggtgaga     300
atccaagcta gcttggcgag attttcagga gctaaggaag ctaaaatgga gaaaaaatc      360 actggatata ccaccgttga tatatcccaa tggcatcgta agaacatttt tgaggcattt     420
cagtcagttg ctcaatgtac ctataaccag accgttcagc tggatattac ggcctttta      480 aagaccgtaa agaaaaataa gcacaagttt tatccggcct ttattcacat tcttgcccgc     540
ctgatgaatg ctcatccgga atttcgtatg gcaatgaaag acggtgagct ggtgatatgg     600
gatagtgttc acccttgtta caccgttttc catgagcaaa ctgaaacgtt ttcatcgctc     660
tggagtgaat accacgacga tttccggcag tttctacaca tatattcgca agatgtggcg     720
tgttacggtg aaaacctggc ctatttccct aaagggttta ttgagaatat gttttttcgtc     780 tcagccaatc cctgggtgag tttcaccagt tttgatttaa acgtggccaa tatggacaac     840
ttcttcgccc cgttttcacc atgggcaaat attatacgca aggcgacaag gtgctgatgc     900
cgctggcgat tcaggttcat catgccgtct gtgatggctt ccatgtcggc agaatgctta     960
atgaattaca acagtactgc gatgagtggc agggcggggc gtaattttttt taaggcagtt    1020 attggtgccc ttaaacgcct ggggtaatga ctctctagct tgaggcatca ataaaaacga    1080
aaggctcagt cgaaagactg ggcctttcgt tttatctgtt gtttgtcggt gaacgctctc    1140
ctgagtagga caaatccgcc gctctagagc tgcctcgcgc gtttcggtga tgacggtgaa    1200
aacctctgac acatgcagct cccggagacg gtcacagctt gtctgtaagc ggatgccggg    1260
agcagacaag cccgtcaggg cgcgtcagcg ggtgttggcg ggtgtcgggg cgcagccatg    1320
acccagtcac gtagcgatag cggagtgtat actggcttaa ctatgcggca tcagagcaga    1380
ttgtactgag agtgcaccat atgcggtgtg aaataccgca cagatgcgta aggagaaaat    1440
accgcatcag gcgctcttcc gcttcctcgc tcactgactc gctgcgctcg gtctgtcggc    1500
tgcggcgagc ggtatcagct cactcaaagg cggtaatacg gttatccaca gaatcagggg    1560
ataacgcagg aaagaacatg tgagcaaaag gccagcaaaa ggccaggaac cgtaaaaagg    1620
ccgcgttgct ggcgtttttc cataggctcc gcccccctga cgagcatcac aaaaatcgac    1680
gctcaagtca gaggtggcga aacccgacag gactataaag ataccaggcg tttccccctg    1740
gaagctccct cgtgcgctct cctgttccga ccctgccgct taccggatac ctgtccgcct    1800
ttctcccttc gggaagcgtg gcgctttctc aatgctcacg ctgtaggtat ctcagttcgg    1860
```

```
tgtaggtcgt tcgctccaag ctgggctgtg tgcacgaacc ccccgttcag cccgaccgct    1920
gcgccttatc cggtaactat cgtcttgagt ccaacccggt aagacacgac ttatcgccac    1980
tggcagcagc cactggtaac aggattagca gagcgaggta tgtaggcggt gctacagagt    2040
tcttgaagtg gtggcctaac tacggctaca ctagaaggac agtatttggt atctgcgctc    2100
tgctgaagcc agttaccttc ggaaaaagag ttggtagctc ttgatccggc aaacaaacca    2160
ccgctggtag cggtggtttt tttgtttgca agcagcagat tacgcgcaga aaaaaggat    2220 ctcaagaaga tcctttgatc ttttctacgg ggtctgacgc tcagtggaac gaaaactcac    2280
gttaagggat tttggtcatg agattatcaa aaggatctt cacctagatc cttttaaatt    2340
aaaaatgaag ttttaaatca atctaaagta tatatgagta acttggtct gacagttacc    2400 aatgcttaat cagtgaggca cctatctcag cgatctgtct atttcgttca tccatagctg    2460
cctgactccc cgtcgtgtag ataactacga tacgggaggg cttaccatct ggccccagtg    2520
ctgcaatgat accgcgagac ccacgctcac cggctccaga tttatcagca ataaaccagc    2580
cagccggaag ggccgagcgc agaagtggtc ctgcaacttt atccgcctcc atccagtcta    2640
ttaattgttg ccgggaagct agagtaagta gttcgccagt taatagtttg cgcaacgttg    2700
ttgccattgc tacaggcatc gtggtgtcac gctcgtcgtt tggtatggct tcattcagct    2760
ccggttccca acgatcaagg cgagttacat gatcccccat gttgtgcaaa aaagcggtta    2820
gctccttcgg tcctccgatc gttgtcagaa gtaagttggc cgcagtgtta tcactcatgg    2880
ttatggcagc actgcataat tctcttactg tcatgccatc cgtaagatgc ttttctgtga    2940
ctggtgagta ctcaaccaag tcattctgag aatagtgtat gcggcgaccg agttgctctt    3000
gcccggcgtc aatacgggat aataccgcgc cacatagcag aactttaaaa gtgctcatca    3060
ttggaaaacg ttcttcgggg cgaaaactct caaggatctt accgctgttg agatccagtt    3120
cgatgtaacc cactcgtgca cccaactgat cttcagcatc ttttactttc accagcgttt    3180
ctgggtgagc aaaaacagga aggcaaaatg ccgcaaaaaa gggaataagg gcgacacgga    3240
aatgttgaat actcatactc ttcctttttc aatattattg aagcatttat cagggttatt    3300
gtctcatgag cggatacata tttgaatgta tttagaaaaa taaacaaata ggggttccgc    3360
gcacatttcc ccgaaaagtg ccacctgacg tctaagaaac cattattatc atgacattaa    3420
cctataaaaa taggcgtatc acgaggccct ttcgtcttca c                       3461

<210> SEQ ID NO 7
<211> LENGTH: 300
<212> TYPE: DNA
<213> ORGANISM: Dengue virus

<400> SEQUENCE: 7
atgaacaacc aacggaaaaa gacggctcga ccgtctttca atatgctgaa acgcgcgaga     60
aaccgcgtgt caactgtttc acagttggcg aagagattct caaaaggatt gctctcaggc    120
caaggaccca tgaaattggt gatggccttc atagcattcc taagatttct agccataccc    180
ccaacagcag gaattttggc tagatggggc tcattcaaga gaatggagc gatcaaagtg    240 ctacggggtt tcaagaaaga aatctcaaac atgttgaata atgaatag aaggaaaaga    300

<210> SEQ ID NO 8
<211> LENGTH: 26
<212> TYPE: DNA
<213> ORGANISM: Dengue Virus

<400> SEQUENCE: 8
```

```
ggatccatga acaaccaacg gaaaaa                                          26

<210> SEQ ID NO 9
<211> LENGTH: 24
<212> TYPE: DNA
<213> ORGANISM: Dengue Virus

<400> SEQUENCE: 9
aagctttctt ttccttctat tcat                                            24

<210> SEQ ID NO 10
<211> LENGTH: 345
<212> TYPE: DNA
<213> ORGANISM: Dengue virus

<400> SEQUENCE: 10
atgagaggat cgcatcacca tcaccatcac ggatccatga acaaccaacg gaaaaagacg     60
gctcgaccgt ctttcaatat gctgaaacgc gcgagaaacc gcgtgtcaac tgtttcacag    120
ttggcgaaga gattctcaaa aggattgctc tcaggccaag gacccatgaa attggtgatg    180
gccttcatag cattcctaag atttctagcc atacccccaa cagcaggaat tttggctaga    240
tggggctcat tcaagaagaa tggagcgatc aaagtgctac ggggtttcaa gaaagaaatc    300
tcaaacatgt tgaatataat gaatagaagg aaaagataaa agctt                    345

<210> SEQ ID NO 11

<400> SEQUENCE: 11

000

<210> SEQ ID NO 12
<211> LENGTH: 426
<212> TYPE: DNA
<213> ORGANISM: Dengue Virus

<400> SEQUENCE: 12
aggctgagaa tggacaaact acagctcaaa ggaatgtcat actctatgtg tacaggaaag     60
tttaaaattg tgaaggaaat agcagaaaca caacatggaa caatagttat cagagtacaa    120
tatgaagggg acggctctcc atgtaagatc ccttttgaga taatggattt ggaaaaaaga    180
cacgtcttag gtcgcctgat tacagttaac ccgatcgtaa cagaaaaaga tagcccagtc    240
aacatagaag cagaacctcc attcggagac agctacatca tcataggagt agagccggga    300
caattgaaac tcaactggtt taagaaagga agttccatcg ccaaatgttg tgagacaaca    360
atgagaggag cgaagagaat ggccatttta ggtgacacag cctgggattt tggaagcctg    420
ggaggg                                                               426

<210> SEQ ID NO 13
<211> LENGTH: 21
<212> TYPE: DNA
<213> ORGANISM: Dengue Virus

<400> SEQUENCE: 13
cttggatcca ttctgagaat g                                               21

<210> SEQ ID NO 14
<211> LENGTH: 33
<212> TYPE: DNA
<213> ORGANISM: Dengue Virus
```

<400> SEQUENCE: 14
tgtggatcct cctcctaggc ttccaaaatc cca                              33

<210> SEQ ID NO 15
<211> LENGTH: 753
<212> TYPE: DNA
<213> ORGANISM: Dengue Virus

<400> SEQUENCE: 15
catcaccatc accatcacgg atccaggctg agaatggaca aactacagct caaaggaatg     60
tcatactcta tgtgtacagg aaagtttaaa attgtgaagg aaatagcaga acacaacat    120
ggaacaatag ttatcagagt acaatatgaa ggggacggct ctccatgtaa gatccctttt    180
gagataatgg atttggaaaa agacacgtc ttaggtcgcc tgattacagt taacccgatc     240
gtaacagaaa agatagcccc agtcaacata gaagcagaac ctccattcgg agacagctac    300
atcatcatag gagtagagcc gggacaattg aaactcaact ggtttaagaa aggaagttcc    360
atcggccaaa tgtttgagac aacaatgaga ggagcgaaga gaatggccat tttaggtgac    420
acagcctggg attttggatc cctgggagga ggatccaata ccaacgaaa aaaggcgaga    480
agtacgcctt caatatgct gaaacgcgag agaaaccgcg tgtcaactgt gcaacagctg    540
acaaagagat tctcacttgg aatgctgcaa ggacgaggac cattaaaact gttcatggcc    600
cttgtggcgt tccttcgttt cctaacaatc ccaccaacag cagggatact gaaaagatgg    660
ggaacgatca aaaaatcaaa agctatcaat gttttgagag ggttcaggaa agagattgga    720
aggatgctga acatcttgaa caggagacgc taa                              753

<210> SEQ ID NO 16
<211> LENGTH: 250
<212> TYPE: PRT
<213> ORGANISM: Dengue Virus

<400> SEQUENCE: 16

His His His His His His Gly Ser Arg Leu Arg Met Asp Lys Leu Gln
1               5                   10                  15

Leu Lys Gly Met Ser Tyr Ser Met Cys Thr Gly Lys Phe Lys Ile Val
            20                  25                  30

Lys Glu Ile Ala Glu Thr Gln His Gly Thr Ile Val Ile Arg Val Gln
        35                  40                  45

Tyr Glu Gly Asp Gly Ser Pro Cys Lys Ile Pro Phe Glu Ile Met Asp
    50                  55                  60

Leu Glu Lys Arg His Val Leu Gly Arg Leu Ile Thr Val Asn Pro Ile
65                  70                  75                  80

Val Thr Glu Lys Asp Ser Pro Val Asn Ile Glu Ala Glu Pro Pro Phe
                85                  90                  95

Gly Asp Ser Tyr Ile Ile Ile Gly Val Glu Pro Gly Gln Leu Lys Leu
            100                 105                 110

Asn Trp Phe Lys Lys Gly Ser Ser Ile Gly Gln Met Phe Glu Thr Thr
        115                 120                 125

Met Arg Gly Ala Lys Arg Met Ala Ile Leu Gly Asp Thr Ala Trp Asp
    130                 135                 140

Phe Gly Ser Leu Gly Gly Gly Ser Asn Asn Gln Arg Lys Lys Ala Arg
145                 150                 155                 160

Ser Thr Pro Phe Asn Met Leu Lys Arg Glu Arg Asn Arg Val Ser Thr
                165                 170                 175

```
Val Gln Gln Leu Thr Lys Arg Phe Ser Leu Gly Met Leu Gln Gly Arg
            180                 185                 190

Gly Pro Leu Lys Leu Phe Met Ala Leu Val Ala Phe Leu Arg Phe Leu
            195                 200                 205

Thr Ile Pro Pro Thr Ala Gly Ile Leu Lys Arg Trp Gly Thr Ile Lys
            210                 215                 220

Lys Ser Lys Ala Ile Asn Val Leu Arg Gly Phe Arg Lys Glu Ile Gly
225                 230                 235                 240

Arg Met Leu Asn Ile Leu Asn Arg Arg
            245                 250

<210> SEQ ID NO 17
<211> LENGTH: 142
<212> TYPE: PRT
<213> ORGANISM: Dengue Virus type 1

<400> SEQUENCE: 17

Arg Leu Lys Met Asp Lys Leu Thr Leu Lys Gly Val Ser Tyr Val Met
1               5                   10                  15

Cys Thr Gly Ser Phe Lys Leu Glu Lys Glu Val Ala Glu Thr Gln His
            20                  25                  30

Gly Thr Val Leu Val Gln Val Lys Tyr Glu Gly Thr Asp Ala Pro Cys
        35                  40                  45

Lys Ile Pro Phe Ser Ser Gln Asp Glu Lys Gly Val Thr Gln Asn Gly
    50                  55                  60

Arg Leu Ile Thr Ala Asn Pro Ile Val Ile Asp Lys Glu Lys Pro Val
65                  70                  75                  80

Asn Ile Glu Ala Glu Pro Pro Phe Gly Glu Ser Tyr Ile Val Val Gly
                85                  90                  95

Ala Gly Glu Lys Ala Leu Lys Leu Ser Trp Phe Lys Lys Gly Ser Ser
            100                 105                 110

Ile Gly Lys Met Phe Glu Ala Thr Ala Arg Gly Ala Arg Arg Met Ala
        115                 120                 125

Ile Leu Gly Asp Thr Ala Trp Asp Phe Gly Ser Ile Gly Gly
    130                 135                 140

<210> SEQ ID NO 18
<211> LENGTH: 142
<212> TYPE: PRT
<213> ORGANISM: Dengue virus type 3

<400> SEQUENCE: 18

Arg Leu Lys Met Asp Lys Leu Glu Leu Lys Gly Met Ser Tyr Ala Met
1               5                   10                  15

Cys Thr Asn Thr Phe Val Leu Lys Lys Glu Val Ser Glu Thr Gln His
            20                  25                  30

Gly Thr Ile Leu Ile Lys Val Glu Tyr Lys Gly Glu Asp Val Pro Cys
        35                  40                  45

Lys Ile Pro Phe Ser Thr Glu Asp Gly Gln Gly Lys Ala His Asn Gly
    50                  55                  60

Arg Leu Ile Thr Ala Asn Pro Val Val Thr Lys Lys Glu Glu Pro Val
65                  70                  75                  80

Asn Ile Glu Ala Glu Pro Pro Phe Gly Glu Ser Asn Ile Val Ile Gly
                85                  90                  95

Ile Gly Asp Asn Ala Leu Lys Ile Asn Trp Tyr Lys Lys Gly Ser Ser
            100                 105                 110
```

```
Ile Gly Lys Met Phe Glu Ala Thr Ala Arg Gly Ala Arg Arg Met Ala
        115                 120                 125

Ile Leu Gly Asp Thr Ala Trp Asp Phe Gly Ser Val Gly Gly
        130                 135                 140

<210> SEQ ID NO 19
<211> LENGTH: 142
<212> TYPE: PRT
<213> ORGANISM: Dengue virus type 4

<400> SEQUENCE: 19

Lys Val Arg Met Glu Lys Leu Arg Ile Lys Gly Met Ser Tyr Thr Met
1               5                   10                  15

Cys Ser Gly Lys Phe Ser Ile Asp Lys Glu Met Ala Glu Thr Gln His
            20                  25                  30

Gly Thr Thr Val Val Lys Val Lys Tyr Glu Gly Ala Gly Ala Pro Cys
        35                  40                  45

Lys Val Pro Ile Glu Ile Arg Asp Val Asn Lys Glu Lys Val Val Gly
    50                  55                  60

Arg Ile Ile Ser Ser Thr Pro Leu Ala Glu Asn Thr Asn Ser Val Thr
65                  70                  75                  80

Asn Ile Glu Leu Glu Pro Pro Phe Gly Asp Ser Tyr Ile Val Ile Gly
                85                  90                  95

Val Gly Asn Ser Ala Leu Thr Leu His Trp Phe Arg Lys Gly Ser Ser
            100                 105                 110

Ile Gly Lys Met Phe Glu Ser Thr Tyr Arg Gly Ala Lys Arg Met Ala
        115                 120                 125

Ile Leu Gly Glu Thr Ala Trp Asp Phe Gly Ser Val Gly Gly
        130                 135                 140

<210> SEQ ID NO 20
<211> LENGTH: 749
<212> TYPE: PRT
<213> ORGANISM: Dengue virus type 1

<400> SEQUENCE: 20

Met Gly His His His His His His Ala Met Val Asp Lys Arg Met Ala
1               5                   10                  15

Leu Val Glu Leu Lys Val Pro Asp Ile Gly Gly His Glu Asn Val Asp
            20                  25                  30

Ile Ile Ala Val Glu Val Asn Val Gly Asp Thr Ile Ala Val Asp Asp
        35                  40                  45

Thr Leu Ile Thr Leu Asp Leu Glu Met Asp Val Pro Ala Glu Val Ala
    50                  55                  60

Gly Val Val Lys Glu Val Lys Val Gly Asp Lys Ile Ser Glu
65                  70                  75                  80

Gly Gly Leu Ile Val Val Glu Ala Glu Gly Thr Ala Ala Pro
                85                  90                  95

Lys Ala Glu Ala Ala Ala Pro Ala Gln Glu Ala Pro Lys Ala Ala
            100                 105                 110

Ala Pro Ala Pro Gln Ala Gln Phe Gly Gly Ser Ala Asp Ala Glu
        115                 120                 125

Tyr Asp Val Val Val Leu Gly Gly Gly Pro Gly Gly Tyr Ser Ala Ala
    130                 135                 140

Phe Ala Ala Ala Asp Glu Gly Leu Lys Val Ala Ile Val Glu Arg Tyr
145                 150                 155                 160
```

-continued

Lys Thr Leu Gly Gly Val Cys Leu Asn Val Gly Cys Ile Pro Ser Lys
                165                 170                 175

Ala Leu Leu His Asn Ala Ala Val Ile Asp Glu Val Arg His Leu Ala
            180                 185                 190

Ala Asn Gly Ile Lys Tyr Pro Glu Pro Glu Leu Asp Ile Asp Met Leu
        195                 200                 205

Arg Ala Tyr Lys Asp Gly Val Val Ser Arg Leu Thr Gly Gly Leu Ala
    210                 215                 220

Gly Met Ala Lys Ser Arg Lys Val Asp Val Ile Gln Gly Asp Gly Gln
225                 230                 235                 240

Phe Leu Asp Pro His His Leu Glu Val Ser Leu Thr Ala Gly Asp Ala
                245                 250                 255

Tyr Glu Gln Ala Ala Pro Thr Gly Glu Lys Lys Ile Val Ala Phe Lys
            260                 265                 270

Asn Cys Ile Ile Ala Ala Gly Ser Arg Val Thr Lys Leu Pro Phe Ile
        275                 280                 285

Pro Glu Asp Pro Arg Ile Ile Asp Ser Ser Gly Ala Leu Ala Leu Lys
    290                 295                 300

Glu Val Pro Gly Lys Leu Leu Ile Ile Gly Gly Ile Ile Gly Leu
305                 310                 315                 320

Glu Met Gly Thr Val Tyr Ser Thr Leu Gly Ser Arg Leu Asp Val Val
                325                 330                 335

Glu Met Met Asp Gly Leu Met Gln Gly Ala Asp Arg Asp Leu Val Lys
            340                 345                 350

Val Trp Gln Lys Gln Asn Glu Tyr Arg Phe Asp Asn Ile Met Val Asn
        355                 360                 365

Thr Lys Thr Val Ala Val Glu Pro Lys Glu Asp Gly Val Tyr Val Thr
    370                 375                 380

Phe Glu Gly Ala Asn Ala Pro Lys Glu Pro Gln Arg Tyr Asp Ala Val
385                 390                 395                 400

Leu Val Ala Ala Gly Arg Ala Pro Asn Gly Lys Leu Ile Ser Ala Glu
                405                 410                 415

Lys Ala Gly Val Ala Val Thr Asp Arg Gly Phe Ile Glu Val Asp Lys
            420                 425                 430

Gln Met Arg Thr Asn Val Pro His Ile Tyr Ala Ile Gly Asp Ile Val
        435                 440                 445

Gly Gln Pro Met Leu Ala His Lys Ala Val His Glu Gly His Val Ala
    450                 455                 460

Ala Glu Asn Cys Ala Gly His Lys Ala Tyr Phe Asp Ala Arg Val Ile
465                 470                 475                 480

Pro Gly Val Ala Tyr Thr Ser Pro Glu Val Ala Trp Val Gly Glu Thr
                485                 490                 495

Glu Leu Ser Ala Lys Ala Ser Gly Arg Lys Ile Thr Lys Ala Asn Phe
            500                 505                 510

Pro Trp Ala Ala Ser Gly Arg Ala Ile Ala Asn Gly Cys Asp Lys Pro
        515                 520                 525

Phe Thr Lys Leu Ile Phe Asp Ala Glu Thr Gly Arg Ile Ile Gly Gly
    530                 535                 540

Gly Ile Val Gly Pro Asn Gly Gly Asp Met Ile Gly Glu Val Cys Leu
545                 550                 555                 560

Ala Ile Glu Met Gly Cys Asp Ala Ala Asp Ile Gly Lys Thr Ile His
                565                 570                 575

```
Pro His Pro Thr Leu Gly Glu Ser Ile Gly Met Ala Ala Glu Val Ala
            580                 585                 590

Leu Gly Thr Cys Thr Asp Leu Pro Pro Gln Lys Lys Lys Gly Ser Arg
        595                 600                 605

Leu Lys Met Asp Lys Leu Thr Leu Lys Gly Val Ser Tyr Val Met Cys
    610                 615                 620

Thr Gly Ser Phe Lys Leu Glu Lys Glu Val Ala Glu Thr Gln His Gly
625                 630                 635                 640

Thr Val Leu Val Gln Val Lys Tyr Glu Gly Thr Asp Ala Pro Cys Lys
            645                 650                 655

Ile Pro Phe Ser Ser Gln Asp Glu Lys Gly Val Thr Gln Asn Gly Arg
        660                 665                 670

Leu Ile Thr Ala Asn Pro Ile Val Ile Asp Lys Glu Lys Pro Val Asn
    675                 680                 685

Ile Glu Ala Glu Pro Pro Phe Gly Glu Ser Tyr Ile Val Val Gly Ala
690                 695                 700

Gly Glu Lys Ala Leu Lys Leu Ser Trp Phe Lys Lys Gly Ser Ser Ile
705                 710                 715                 720

Gly Lys Met Phe Glu Ala Thr Ala Arg Gly Ala Arg Arg Met Ala Ile
            725                 730                 735

Leu Gly Asp Thr Ala Trp Asp Phe Gly Ser Ile Gly Gly
            740                 745

<210> SEQ ID NO 21
<211> LENGTH: 749
<212> TYPE: PRT
<213> ORGANISM: Dengue virus type 3

<400> SEQUENCE: 21

Met Gly His His His His His His Ala Met Val Asp Lys Arg Met Ala
1               5                   10                  15

Leu Val Glu Leu Lys Val Pro Asp Ile Gly Gly His Glu Asn Val Asp
            20                  25                  30

Ile Ile Ala Val Glu Val Asn Val Gly Asp Thr Ile Ala Val Asp Asp
        35                  40                  45

Thr Leu Ile Thr Leu Asp Leu Glu Met Asp Val Pro Ala Glu Val Ala
    50                  55                  60

Gly Val Val Lys Glu Val Lys Val Lys Val Gly Asp Lys Ile Ser Glu
65                  70                  75                  80

Gly Gly Leu Ile Val Val Glu Ala Glu Gly Thr Ala Ala Ala Pro
            85                  90                  95

Lys Ala Glu Ala Ala Ala Pro Ala Gln Glu Ala Pro Lys Ala Ala
                100                 105                 110

Ala Pro Ala Pro Gln Ala Ala Gln Phe Gly Gly Ser Ala Asp Ala Glu
        115                 120                 125

Tyr Asp Val Val Leu Gly Gly Pro Gly Gly Tyr Ser Ala Ala
    130                 135                 140

Phe Ala Ala Ala Asp Glu Gly Leu Lys Val Ala Ile Val Glu Arg Tyr
145                 150                 155                 160

Lys Thr Leu Gly Gly Val Cys Leu Asn Val Gly Cys Ile Pro Ser Lys
            165                 170                 175

Ala Leu Leu His Asn Ala Ala Val Ile Asp Glu Val Arg His Leu Ala
        180                 185                 190

Ala Asn Gly Ile Lys Tyr Pro Glu Pro Glu Leu Asp Ile Asp Met Leu
    195                 200                 205
```

```
Arg Ala Tyr Lys Asp Gly Val Ser Arg Leu Thr Gly Gly Leu Ala
    210                 215                 220
Gly Met Ala Lys Ser Arg Lys Val Asp Val Ile Gln Gly Asp Gly Gln
225                 230                 235                 240
Phe Leu Asp Pro His His Leu Glu Val Ser Leu Thr Ala Gly Asp Ala
                    245                 250                 255
Tyr Glu Gln Ala Ala Pro Thr Gly Glu Lys Lys Ile Val Ala Phe Lys
                260                 265                 270
Asn Cys Ile Ile Ala Ala Gly Ser Arg Val Thr Lys Leu Pro Phe Ile
            275                 280                 285
Pro Glu Asp Pro Arg Ile Ile Asp Ser Ser Gly Ala Leu Ala Leu Lys
290                 295                 300
Glu Val Pro Gly Lys Leu Leu Ile Ile Gly Gly Ile Ile Gly Leu
305                 310                 315                 320
Glu Met Gly Thr Val Tyr Ser Thr Leu Gly Ser Arg Leu Asp Val Val
                325                 330                 335
Glu Met Met Asp Gly Leu Met Gln Gly Ala Asp Arg Asp Leu Val Lys
            340                 345                 350
Val Trp Gln Lys Gln Asn Glu Tyr Arg Phe Asp Asn Ile Met Val Asn
        355                 360                 365
Thr Lys Thr Val Ala Val Glu Pro Lys Glu Asp Gly Val Tyr Val Thr
    370                 375                 380
Phe Glu Gly Ala Asn Ala Pro Lys Glu Pro Gln Arg Tyr Asp Ala Val
385                 390                 395                 400
Leu Val Ala Ala Gly Arg Ala Pro Asn Gly Lys Leu Ile Ser Ala Glu
                405                 410                 415
Lys Ala Gly Val Ala Val Thr Asp Arg Gly Phe Ile Glu Val Asp Lys
                420                 425                 430
Gln Met Arg Thr Asn Val Pro His Ile Tyr Ala Ile Gly Asp Ile Val
            435                 440                 445
Gly Gln Pro Met Leu Ala His Lys Ala Val His Glu Gly His Val Ala
        450                 455                 460
Ala Glu Asn Cys Ala Gly His Lys Ala Tyr Phe Asp Ala Arg Val Ile
465                 470                 475                 480
Pro Gly Val Ala Tyr Thr Ser Pro Glu Val Ala Trp Val Gly Glu Thr
                485                 490                 495
Glu Leu Ser Ala Lys Ala Ser Gly Arg Lys Ile Thr Lys Ala Asn Phe
            500                 505                 510
Pro Trp Ala Ala Ser Gly Arg Ala Ile Ala Asn Gly Cys Asp Lys Pro
        515                 520                 525
Phe Thr Lys Leu Ile Phe Asp Ala Glu Thr Gly Arg Ile Ile Gly Gly
    530                 535                 540
Gly Ile Val Gly Pro Asn Gly Gly Asp Met Ile Gly Glu Val Cys Leu
545                 550                 555                 560
Ala Ile Glu Met Gly Cys Asp Ala Ala Asp Ile Gly Lys Thr Ile His
                565                 570                 575
Pro His Pro Thr Leu Gly Glu Ser Ile Gly Met Ala Ala Glu Val Ala
            580                 585                 590
Leu Gly Thr Cys Thr Asp Leu Pro Pro Gln Lys Lys Gly Ser Arg
        595                 600                 605
Leu Lys Met Asp Lys Leu Lys Leu Lys Gly Met Ser Tyr Ala Met Cys
    610                 615                 620
```

```
Leu Asn Thr Phe Val Leu Lys Lys Glu Val Ser Glu Thr Gln His Gly
625                 630                 635                 640

Thr Ile Leu Ile Lys Val Glu Tyr Lys Gly Glu Asp Ala Pro Cys Lys
            645                 650                 655

Ile Pro Phe Ser Thr Glu Asp Gly Gln Gly Lys Ala His Asn Gly Arg
        660                 665                 670

Leu Ile Thr Ala Asn Pro Val Val Thr Lys Lys Glu Glu Pro Val Asn
    675                 680                 685

Ile Glu Ala Glu Pro Pro Phe Gly Glu Ser Asn Ile Val Ile Gly Ile
690                 695                 700

Gly Asp Lys Ala Leu Lys Ile Asn Trp Tyr Arg Lys Gly Ser Ser Ile
705                 710                 715                 720

Gly Lys Met Phe Glu Ala Thr Ala Arg Gly Ala Arg Arg Met Ala Ile
            725                 730                 735

Leu Gly Asp Thr Ala Trp Asp Phe Gly Ser Val Gly Gly
            740                 745

<210> SEQ ID NO 22
<211> LENGTH: 749
<212> TYPE: PRT
<213> ORGANISM: Dengue virus type 4

<400> SEQUENCE: 22

Met Gly His His His His His His Ala Met Val Asp Lys Arg Met Ala
1               5                   10                  15

Leu Val Glu Leu Lys Val Pro Asp Ile Gly Gly His Glu Asn Val Asp
            20                  25                  30

Ile Ile Ala Val Glu Val Asn Val Gly Asp Thr Ile Ala Val Asp Asp
        35                  40                  45

Thr Leu Ile Thr Leu Asp Leu Glu Met Asp Val Pro Ala Glu Val Ala
    50                  55                  60

Gly Val Val Lys Glu Val Lys Val Lys Val Gly Asp Lys Ile Ser Glu
65                  70                  75                  80

Gly Gly Leu Ile Val Val Glu Ala Glu Gly Thr Ala Ala Ala Ala Pro
            85                  90                  95

Lys Ala Glu Ala Ala Ala Pro Ala Gln Glu Ala Pro Lys Ala Ala
            100                 105                 110

Ala Pro Ala Pro Gln Ala Ala Gln Phe Gly Gly Ser Ala Asp Ala Glu
        115                 120                 125

Tyr Asp Val Val Val Leu Gly Gly Pro Gly Gly Tyr Ser Ala Ala
    130                 135                 140

Phe Ala Ala Ala Asp Glu Gly Leu Lys Val Ala Ile Val Glu Arg Tyr
145                 150                 155                 160

Lys Thr Leu Gly Gly Val Cys Leu Asn Val Gly Cys Ile Pro Ser Lys
            165                 170                 175

Ala Leu Leu His Asn Ala Ala Val Ile Asp Glu Val Arg His Leu Ala
        180                 185                 190

Ala Asn Gly Ile Lys Tyr Pro Glu Pro Glu Leu Asp Ile Asp Met Leu
    195                 200                 205

Arg Ala Tyr Lys Asp Gly Val Val Ser Arg Leu Thr Gly Gly Leu Ala
210                 215                 220

Gly Met Ala Lys Ser Arg Lys Val Asp Val Ile Gln Gly Asp Gly Gln
225                 230                 235                 240

Phe Leu Asp Pro His His Leu Glu Val Ser Leu Thr Ala Gly Asp Ala
            245                 250                 255
```

```
Tyr Glu Gln Ala Ala Pro Thr Gly Glu Lys Lys Ile Val Ala Phe Lys
            260                 265                 270
Asn Cys Ile Ile Ala Ala Gly Ser Arg Val Thr Lys Leu Pro Phe Ile
            275                 280                 285
Pro Glu Asp Pro Arg Ile Ile Asp Ser Ser Gly Ala Leu Ala Leu Lys
290                 295                 300
Glu Val Pro Gly Lys Leu Leu Ile Ile Gly Gly Ile Ile Gly Leu
305                 310                 315                 320
Glu Met Gly Thr Val Tyr Ser Thr Leu Gly Ser Arg Leu Asp Val Val
                325                 330                 335
Glu Met Met Asp Gly Leu Met Gln Gly Ala Asp Arg Asp Leu Val Lys
            340                 345                 350
Val Trp Gln Lys Gln Asn Glu Tyr Arg Phe Asp Asn Ile Met Val Asn
            355                 360                 365
Thr Lys Thr Val Ala Val Glu Pro Lys Glu Asp Gly Val Tyr Val Thr
        370                 375                 380
Phe Glu Gly Ala Asn Ala Pro Lys Glu Pro Gln Arg Tyr Asp Ala Val
385                 390                 395                 400
Leu Val Ala Ala Gly Arg Ala Pro Asn Gly Lys Leu Ile Ser Ala Glu
                405                 410                 415
Lys Ala Gly Val Ala Val Thr Asp Arg Gly Phe Ile Glu Val Asp Lys
            420                 425                 430
Gln Met Arg Thr Asn Val Pro His Ile Tyr Ala Ile Gly Asp Ile Val
            435                 440                 445
Gly Gln Pro Met Leu Ala His Lys Ala Val His Glu Gly His Val Ala
        450                 455                 460
Ala Glu Asn Cys Ala Gly His Lys Ala Tyr Phe Asp Ala Arg Val Ile
465                 470                 475                 480
Pro Gly Val Ala Tyr Thr Ser Pro Glu Val Ala Trp Val Gly Glu Thr
                485                 490                 495
Glu Leu Ser Ala Lys Ala Ser Gly Arg Lys Ile Thr Lys Ala Asn Phe
            500                 505                 510
Pro Trp Ala Ala Ser Gly Arg Ala Ile Ala Asn Gly Cys Asp Lys Pro
        515                 520                 525
Phe Thr Lys Leu Ile Phe Asp Ala Glu Thr Gly Arg Ile Ile Gly Gly
            530                 535                 540
Gly Ile Val Gly Pro Asn Gly Gly Asp Met Ile Gly Glu Val Cys Leu
545                 550                 555                 560
Ala Ile Glu Met Gly Cys Asp Ala Ala Asp Ile Gly Lys Thr Ile His
                565                 570                 575
Pro His Pro Thr Leu Gly Glu Ser Ile Gly Met Ala Ala Glu Val Ala
            580                 585                 590
Leu Gly Thr Cys Thr Asp Leu Pro Pro Gln Lys Lys Gly Ser Lys
            595                 600                 605
Val Arg Met Glu Lys Leu Arg Ile Lys Gly Met Ser Tyr Thr Met Cys
        610                 615                 620
Ser Gly Lys Phe Ser Ile Asp Lys Glu Met Ala Glu Thr Gln His Gly
625                 630                 635                 640
Thr Thr Val Val Lys Val Lys Tyr Glu Gly Ala Gly Ala Pro Cys Lys
                645                 650                 655
Val Pro Ile Glu Ile Arg Asp Val Asn Lys Glu Lys Val Val Gly Arg
            660                 665                 670
```

-continued

```
Ile Ile Ser Ser Thr Pro Leu Ala Glu Asn Thr Asn Ser Val Thr Asn
        675                 680                 685

Ile Glu Leu Glu Pro Pro Phe Gly Asp Ser Tyr Ile Val Ile Gly Val
        690                 695                 700

Gly Asn Ser Ala Leu Thr Leu His Trp Phe Arg Lys Gly Ser Ser Ile
705                 710                 715                 720

Gly Lys Met Phe Glu Ser Thr Tyr Arg Gly Ala Lys Arg Met Ala Ile
                725                 730                 735

Leu Gly Glu Thr Ala Trp Asp Phe Gly Ser Val Gly Gly
                740                 745

<210> SEQ ID NO 23
<211> LENGTH: 750
<212> TYPE: PRT
<213> ORGANISM: Dengue virus type 2

<400> SEQUENCE: 23

Met Gly His His His His His His Ala Met Val Asp Lys Arg Met Ala
1               5                   10                  15

Leu Val Glu Leu Lys Val Pro Asp Ile Gly Gly His Glu Asn Val Asp
            20                  25                  30

Ile Ile Ala Val Glu Val Asn Val Gly Asp Thr Ile Ala Val Asp Asp
        35                  40                  45

Thr Leu Ile Thr Leu Asp Leu Glu Met Asp Val Pro Ala Glu Val Ala
    50                  55                  60

Gly Val Val Lys Glu Val Lys Val Lys Val Gly Asp Lys Ile Ser Glu
65                  70                  75                  80

Gly Gly Leu Ile Val Val Glu Ala Glu Gly Thr Ala Ala Ala Ala Pro
                85                  90                  95

Lys Ala Glu Ala Ala Ala Pro Ala Gln Glu Ala Pro Lys Ala Ala
            100                 105                 110

Ala Pro Ala Pro Gln Ala Ala Gln Phe Gly Gly Ser Ala Asp Ala Glu
        115                 120                 125

Tyr Asp Val Val Val Leu Gly Gly Gly Pro Gly Gly Tyr Ser Ala Ala
    130                 135                 140

Phe Ala Ala Ala Asp Glu Gly Leu Lys Val Ala Ile Val Glu Arg Tyr
145                 150                 155                 160

Lys Thr Leu Gly Gly Val Cys Leu Asn Val Gly Cys Ile Pro Ser Lys
                165                 170                 175

Ala Leu Leu His Asn Ala Ala Val Ile Asp Glu Val Arg His Leu Ala
            180                 185                 190

Ala Asn Gly Ile Lys Tyr Pro Glu Pro Glu Leu Asp Ile Asp Met Leu
        195                 200                 205

Arg Ala Tyr Lys Asp Gly Val Val Ser Arg Leu Thr Gly Gly Leu Ala
    210                 215                 220

Gly Met Ala Lys Ser Arg Lys Val Asp Val Ile Gln Gly Asp Gly Gln
225                 230                 235                 240

Phe Leu Asp Pro His His Leu Glu Val Ser Leu Thr Ala Gly Asp Ala
                245                 250                 255

Tyr Glu Gln Ala Ala Pro Thr Gly Glu Lys Lys Ile Val Ala Phe Lys
            260                 265                 270

Asn Cys Ile Ile Ala Ala Gly Ser Arg Val Thr Lys Leu Pro Phe Ile
        275                 280                 285

Pro Glu Asp Pro Arg Ile Ile Asp Ser Ser Gly Ala Leu Ala Leu Lys
    290                 295                 300
```

-continued

```
Glu Val Pro Gly Lys Leu Leu Ile Ile Gly Gly Ile Ile Gly Leu
305                 310                 315                 320

Glu Met Gly Thr Val Tyr Ser Thr Leu Gly Ser Arg Leu Asp Val Val
                    325                 330                 335

Glu Met Met Asp Gly Leu Met Gln Gly Ala Asp Arg Asp Leu Val Lys
                340                 345                 350

Val Trp Gln Lys Gln Asn Glu Tyr Arg Phe Asp Asn Ile Met Val Asn
            355                 360                 365

Thr Lys Thr Val Ala Val Glu Pro Lys Glu Asp Gly Val Tyr Val Thr
        370                 375                 380

Phe Glu Gly Ala Asn Ala Pro Lys Glu Pro Gln Arg Tyr Asp Ala Val
385                 390                 395                 400

Leu Val Ala Ala Gly Arg Ala Pro Asn Gly Lys Leu Ile Ser Ala Glu
                    405                 410                 415

Lys Ala Gly Val Ala Val Thr Asp Arg Gly Phe Ile Glu Val Asp Lys
                420                 425                 430

Gln Met Arg Thr Asn Val Pro His Ile Tyr Ala Ile Gly Asp Ile Val
            435                 440                 445

Gly Gln Pro Met Leu Ala His Lys Ala Val His Glu Gly His Val Ala
        450                 455                 460

Ala Glu Asn Cys Ala Gly His Lys Ala Tyr Phe Asp Ala Arg Val Ile
465                 470                 475                 480

Pro Gly Val Ala Tyr Thr Ser Pro Glu Val Ala Trp Val Gly Glu Thr
                    485                 490                 495

Glu Leu Ser Ala Lys Ala Ser Gly Arg Lys Ile Thr Lys Ala Asn Phe
                500                 505                 510

Pro Trp Ala Ala Ser Gly Arg Ala Ile Ala Asn Gly Cys Asp Lys Pro
            515                 520                 525

Phe Thr Lys Leu Ile Phe Asp Ala Glu Thr Gly Arg Ile Ile Gly Gly
        530                 535                 540

Gly Ile Val Gly Pro Asn Gly Gly Asp Met Ile Gly Glu Val Cys Leu
545                 550                 555                 560

Ala Ile Glu Met Gly Cys Asp Ala Ala Asp Ile Gly Lys Thr Ile His
                    565                 570                 575

Pro His Pro Thr Leu Gly Glu Ser Ile Gly Met Ala Ala Glu Val Ala
                580                 585                 590

Leu Gly Thr Cys Thr Asp Leu Pro Pro Gln Lys Lys Gly Ser Asp
            595                 600                 605

Arg Leu Arg Met Asp Lys Leu Gln Leu Lys Gly Met Ser Tyr Ser Met
        610                 615                 620

Cys Thr Gly Lys Phe Lys Ile Val Lys Glu Ile Ala Glu Thr Gln His
625                 630                 635                 640

Gly Thr Ile Val Ile Arg Val Gln Tyr Glu Gly Asp Gly Ser Pro Cys
                    645                 650                 655

Lys Ile Pro Phe Glu Ile Met Asp Leu Glu Lys Arg His Val Leu Gly
                660                 665                 670

Arg Leu Ile Thr Val Asn Pro Ile Val Thr Glu Lys Asp Ser Pro Val
            675                 680                 685

Asn Ile Glu Ala Glu Pro Pro Phe Gly Asp Ser Tyr Ile Ile Ile Gly
        690                 695                 700

Val Glu Pro Gly Gln Leu Lys Leu Asn Trp Phe Lys Lys Gly Ser Ser
705                 710                 715                 720
```

-continued

```
Ile Gly Gln Met Phe Glu Thr Thr Met Arg Gly Ala Lys Arg Met Ala
                725                 730                 735
Ile Leu Gly Asp Thr Ala Trp Asp Phe Gly Ser Leu Gly Gly
            740                 745                 750

<210> SEQ ID NO 24
<211> LENGTH: 142
<212> TYPE: PRT
<213> ORGANISM: Dengue Virus type 2

<400> SEQUENCE: 24

Arg Leu Arg Met Asp Lys Leu Gln Leu Lys Gly Met Ser Tyr Ser Met
1               5                   10                  15
Cys Thr Gly Lys Phe Lys Ile Val Lys Glu Ile Ala Glu Thr Gln His
                20                  25                  30
Gly Thr Ile Val Ile Arg Val Gln Tyr Glu Gly Asp Gly Ser Pro Cys
            35                  40                  45
Lys Ile Pro Phe Glu Ile Met Asp Leu Glu Lys Arg His Val Leu Gly
    50                  55                  60
Arg Leu Ile Thr Val Asn Pro Ile Val Thr Glu Lys Asp Ser Pro Val
65                  70                  75                  80
Asn Ile Glu Ala Glu Pro Pro Phe Gly Asp Ser Tyr Ile Ile Ile Gly
                85                  90                  95
Val Glu Pro Gly Gln Leu Lys Leu Asn Trp Phe Lys Lys Gly Ser Ser
            100                 105                 110
Ile Gly Gln Met Phe Glu Thr Thr Met Arg Gly Ala Lys Arg Met Ala
        115                 120                 125
Ile Leu Gly Asp Thr Ala Trp Asp Phe Gly Ser Leu Gly Gly
        130                 135                 140
```

PHARMACEUTICAL COMPOUND CAPABLE OF INDUCE IMMUNE PROTECTIVE RESPONSE AGAINST DENGUE VIRUS HAVING THE CAPSID PROTEIN OF THE DENGUE VIRUS

This application is the U.S. National Phase of, and Applicants claim priority from, International Application Number PCT/CU2006/000008 filed 18 Sep. 2006 and Cuban Application bearing Serial No. CU2005-0168 filed 16 Sep. 2005, which are incorporated herein by reference.

The present invention is related to the field of biotechnology and the pharmaceutical industry, in particular to the obtaining of proteins capable of inducing an immune response against the infection with Dengue virus, quoted from now on as DEN, while avoiding the antibody-dependent enhancement phenomenon that has been described in persons re-infected with this virus.

Dengue fever (DF) and dengue hemorrhagic fever (DHF) acquire increasing importance as health problems, affecting several countries of the tropical and subtropical zones of the planet. Dengue virus has been recognized in more than 100 countries and 2 500 million people living in risk areas are estimated. Between 50 and 100 million cases from DF and 250 000 to 500 000 of DHF are reported each year. (Guzmán M. G. and Kouri G. 2002. Dengue: an update. Lancet Infect. Dis. 2: 33-42).

The causal agent of this disease is the Dengue virus of the genus *Flavivirus*, family Flaviviridae, which is transmitted by the mosquito *Aedes aegypti* (Leyssen P., De Clerco E., Neyts J. 2000. Perspectives for the treatment of infections with Flaviviridae. Clin. Microbiol. Rev. 13: 67-82).

Until now four serotypes have been reported that can circulate in a same region. Dengue virus is an RNA positive coated virus, whose genome contains only one reading frame. This RNA is translated in a polyprotein that is processed in three structural proteins and seven non-structural proteins. (Russell P. K., Brandt W. E., Dalrymple J. M. 1980. Chemical and antigenic structure of flaviviruses. The togaviruses: biology, structure, replication. Schelesinger R. W. (ed.). 503-529).

Multiple epidemiological studies have been made to determine the risk factors that entail to the most severe form of Dengue disease. This is characterized by high fever, extrusion of liquids, hemorrhages and finally the Dengue shock. (Gubler D. J. 1998. Dengue and Dengue Hemorrhagic Fever. Clin. Microbiol. Rev. 11: 480-496). One of the most important risk factors is the secondary infection by a heterologous serotype. Cross-protection among the infections of the different serotypes does not exist. (Kouri G., Guzman M. G., Bravo J., Trina C. 1989. Dengue hemorrhagic fever/dengue shock syndrome: lessons from the Cuban epidemic. WHO Bulletin OMS. 67: 375-380).

Several hypotheses exist to explain this phenomenon. One of the most important is the antibody depend enhancement. (Halstead S. B., Scanlon J. E., Umpaivit P., Udomsakdi S. 1969. Dengue and Chikungunya virus infection in man in Thailand, 1962-1964. IV. Epidemiologic studies in the Bangkok metropolitan area. Am. J. Trop. Med. Hyg. 18: 997-1021).

From the first studies, it was raised that DEN virus replicates in greater measurement in peripheral mononuclear cells from the blood of patients who had undergone a previous infection with the virus (Halstead S. B., O'Rourke E. J., Allison A. C. 1977. Dengue viruses and mononuclear phagocytes. II. Identity of blood and tissue leukocytes supporting in vitro infection. J. Exp. Med. 146: 218-229). Later, it was demonstrated that the residual antibodies were the responsables of this effect (Morens D M, Halstead S B, Marchette N J. 1987. Profiles of antibody-dependent enhancement of dengue virus type 2 infection. Microb Pathog. October; 3(4):231-7).

In conditions of specificity or concentration of antibodies in which there is not neutralization, the antibody-virus complexes can be internalized by cells presenting Fcy receptors in the membranes, like monocytes and macrophages. This mechanism, known as antibodies-dependent enhancement (ADE) occurs during secondary infections. (Morens D M, Halstead S B, Marchette N J. 1987. Profiles of antibody-dependent enhancement of dengue virus type 2 infection. Microb Pathog. October; 3(4):231-7; Kliks S. C., Nimmannitya S., Nisalak A., Burke D. S. 1988. Evidence that maternal dengue antibodies are important in the development of dengue hemorrhagic fever in infants. Am. J. Trop. Med. Hyg. 38: 411-419).

Halstead et al. (Halstead S. B., Scanlon J. E., Umpaivit P., Udomsakdi S. 1969. Dengue and Chikungunya virus infection in man in Thailand, 1962-1964. IV. Epidemiologic studies in the Bangkok metropolitan area. Am. J. Trop. Med. Hyg. 18: 997-1021.), in a 3-year study in Bangkok, Thailand, reported that the hospitalization indices by DEN infection among children, reached a maximum in those between 7 and 8 months old. These indices were four to eight times greater than the observed between children of 1-3 months and twice than that in children of 3 years. Kliks et al. (Kliks S. C., Nimmannitya S., Nisalak A., Burke D. S. 1988. Evidence that maternal dengue antibodies are important in the development of dengue hemorrhagic fever in infants. Am. J. Trop. Med. Hyg. 38: 411-419), determined the relation between the maternal neutralizing antibody titers against DEN-2 and the ages of thirteen children with FHD caused by the infection with the homologous virus. The results showed that the infection serious cases with the virus occurred when the maternal antibody levels diminished to sub-neutralizing levels. These data are consistent with the hypothesis in which the maternal antibodies play the double role of protecting first and stimulate the development of DHF later on.

Despite this immunological phenomenon, nowadays the most advanced vaccine candidates worldwide are based in attenuated virus of the different four serotypes, containing the envelope protein. These candidates are able to induce potential amplifying antibodies against the exposed proteins (PrM/M and Envelope) and protector neutralizing antibodies against the four viral serotypes in human volunteers. (Kanesa-thasan N., Sun W., Kim-Ahn G., Van Albert S., Putnak J. R., King A., Raengsakulsrach B., Christ-Schmidt H., Gilson K., Zahradnik J. M., Vaughn D. W., Innis B. L., Saluzzo J. F. y Hoke C. H. 2001. Safety and immunogenicity of attenuated dengue virus vaccines (Aventis Pasteur) in human volunteers. Vaccine. 19: 3179-3188).

High levels of neutralizing antibodies after immunization could prevent the viral replication despite the induction of enhancing antibodies. The problem can take place when the total seroconversion to the four serotypes in the vaccines, in terms of neutralizing Abs, is not obtained or is diminished to low levels in blood and the individuals would become then susceptible to a severe secondary infection with a viral serotype whose protective antibodies are not present. In fact, several tests in monkeys and humans have been made to define the viral amounts in the vaccine formulations. (Guirakhoo F., Arroyo J., Pugachev K. V., Miller C., Zhang Z.-X., Weltzin R., Georgakopoulos K., Catalan J., Ocran S., Soike K., Raterree M., Monath T. P. 2001. Construction, safety, and immunogenicity in nonhuman primates of a chimeric yellow fever-dengue virus tetravalent vaccine. J. Virol. 75: 7290-7304).

In some cases the balance of seroconversion has not been obtained to the four serotypes (Sabchareon A, Lang J, Chanthavanich P, Yoksan S, Forrat R, Attanath P, Sirivichayakul C, Pengsaa K, Pojjaroen-Anant C, Chokejindachai W, Jagsudec A, Saluzzo J F, Bhamarapravati N. 2002. Safety and immunogenicity of tetravalent live-attenuated dengue vaccines in Thai adult volunteers: role of serotype concentration, ratio, and multiple doses. Am J Trop Med Hyg. 66(3): 264-72). In addition, it has been necessary to administer up to three doses of attenuated vaccines in children for a total seroconversion, in terms of neutralizing antibodies and still not known whether these will last in the time (Sabchareon A, Lang J, Chanthavanich P, Yoksan S, Forrat R, Attanath P, Sirivichayakul C, Pengsaa K, Pojjaroen-Anant C, Chambonneau L, Saluzzo J F, Bhamarapravati N. 2004. Safety and immunogenicity of a three dose regimen of two tetravalent live-attenuated dengue vaccines in five- to twelve-year-old Thai children. Pediatr Infect Dis J.; 23(2):99-109). This is one of the most questionable concerns in the vaccine formulations that include the envelope protein of Dengue virus, consequently of the vaccines candidates in development.

Another drawback of the attenuated vaccines, currently in phase I/II, is the safety. Upon the first dose the existence of adverse effects in adults and children like fever, myalgia, petequias and headache, has been demonstrated in several studies (Sabchareon A, Lang J, Chanthavanich P, Yoksan S, Forrat R, Attanath P, Sirivichayakul C, Pengsaa K, Pojjaroen-Anant C, Chambonneau L, Saluzzo J F, Bhamarapravati N. 2004. Safety and immunogenicity of a three dose regimen of two tetravalent live-attenuated dengue vaccines in five- to twelve-year-old Thai children. Pediatr Infect Dis J.; 23(2):99-109). In general the phenomenon of reversion to the virulence potentially associated to live vaccines may be presented.

In the search of new alternatives, it has been developed different variants of vaccine candidates based on the envelope protein or fragments of this one, obtained through a recombinant way. These recombinant candidates avoid the safety problems related to the inoculation of live virus, and are able to sensitize the individual if a balanced response against the four serotypes is not induced (Velzing J, Groen J, Drouet M T, van Amerongen G, Copra C, Osterhaus A D, Deubel V. 1999. Induction of protective immunity against Dengue virus type 2: comparison of candidate live attenuated and recombinant vaccines. Vaccine. March 17; 17(11-12):1312-20). On the other hand, these candidates require powerful adjuvants—not approved for their use in humans yet—to stimulate a serotype-specific suitable protective immune response (Hermida L, Rodriguez R, Lazo L, Silva R, Zulueta A, Chinea G, Lopez C, Guzman M G, Guillen G. 2004. A dengue-2 Envelope fragment inserted within the structure of the P64k meningococcal protein carrier enables a functional immune response against the virus in mice. J Virol Methods. 2004 January; 115(1):41-9).

The humoral response of neutralizing antibodies has been extensively studied in animals and its protector effect has been demonstrated. The cytotoxic cellular immune response as a protector mechanism in Dengue has not deeply been explored. On the contrary, there are several reports in which the correlation between the induction of a cellular response and the most severe form of the disease is demonstrated (Rothman A. L. y Ennis F. A. 1999. Immunopathogenesis of Dengue Hemorragic Fever. Virology. 257: 1-6). These studies are based on the presence of high levels of activated T-cells in those individuals that exhibit DHF (Green S, Pichyangkul S, Vaughn D W, Kalayanarooj S, Nimmannitya S, Nisalak A, Kurane I. Rothman A L, Ennis F A. 1999. Early CD69 expression on peripheral blood lymphocytes from children with dengue hemorrhagic fever. J Infect Dis. 180(5):1429-35).

T-cells epitopes have been reported mainly in nonstructural proteins (Kurane I, Zeng L, Brinton M A, Ennis F A. 1998. Definition of an epitope on NS3 recognized by human CD4+ cytotoxic T lymphocyte clones cross-reactive for dengue virus types 2, 3, and 4. Virology. 1998 Jan. 20; 240(2):169-74), but also are present in the envelope and in the capsid proteins (Bukowski, J. F., I. Kurane, C.-J. Lai, M. Bray, B. Falgout, and F. A. Ennis. 1989. Dengue virus-specific cross-reactive CD8 human cytotoxic T lymphocytes. J. Virol. 63:5086-5091; Gagnon S. J., Zeng W., Kurane I., Ennis F. A. 1996. Identification of two epitopes on the dengue 4 virus capsid protein recognized by a serotype-specific and a panel of serotype-cross-reactive human CD4+ cytotoxic T-lymphocyte clones. J Virol. 70: 141-147). Nevertheless, the protective character of some of these proteins based only on the induction of a cellular immune response has not been demonstrated.

In the search of vaccine candidates that avoid the immunoenhancement phenomenon. studies using the non-structural proteins NS1 and NS3 have been made. In the case of NS1, some level of protection in mice immunized with the recombinant protein has been reached.

Similar results have been obtained using a naked DNA containing the NS1 gene, through the ADCC mechanism (Wu S F. Liao C L, Lin Y L, Yeh C T, Chen L K, Huang Y F, Chou H Y, Huang J L, Shaio M F, Sytwu H K. 2003. Evaluation of protective efficacy and immune mechanisms of using a non-structural protein NS1 in DNA vaccine against dengue 2 virus in mice. Vaccine. September 8; 21(25-26):3919-29). Nevertheless, reports of their possible roll in phenomena of autoimmunity due to the induction of antibodies that recognize human endothelial cells exist (Chiou-Feng Lin, Huan-Yao Lei, Ai-Li Shiau, Hsiao-Sheng Liu, Trai-Ming Yeh, Shun-Hua Chen, Ching-Chuan Liu, Shu-Chen Chiu, and Yee-Shin Lin. 2002. Endothelial Cell Apoptosis Induced by Antibodies against Dengue Virus nonstructural Protein 1 via Production of Nitric Oxide. J. Immunol. 657-664). Additionally, there is a report of protection using a naked DNA formulation containing the NS3 gene; however, it was demonstrated that this protection was mediated by the raised antibodies since the same protection using passive immunization was obtained (Tan C H, Yap E H, Singh M, Deubel V, Chan Y C. 1990. Passive protection studies in mice with monoclonal antibodies directed against the non-structural protein NS3 of dengue 1 virus. J Gen Virol. 1990 March; 71 (Pt 3):745-9). In addition, it is worth noting the hypothesis, that the cellular response can be potentially harmful facing an infection with heterologous virus based on studies of NS3 protein epitopes (Zivny J, DeFronzo M, Jarry W, Jameson J, Cruz J, Ennis F A, Rothman A L. 1999. Partial agonist effect influences the CTL response to a heterologous dengue virus serotype. J Immunol. September 1; 163(5):2754-60).

In the case of the capsid protein of dengue virus, no evidences of protection in the challenge with a lethal dengue virus are reported. Concerning related flaviviruses, a report was published where authors inoculated mice with a naked DNA formulation containing the gene of the Japanese Encephalitis (JE) capsid protein. This formulation did not induce a protective response against the challenge with lethal JE in mice, despite the demonstration of a cytotoxic response (Konishi E, Ajiro N, Nukuzuma C, Mason P W, Kurane I. 2003. Comparison of protective efficacies of plasmid DNAs encoding Japanese encephalitis virus proteins that induce neutralizing antibody or cytotoxic T lymphocytes in mice. Vaccine. September 8; 21(25-26):3675-83).

Protection using the recombinant protein capsid has been demonstrated only in the case of human papilloma virus. However it has been suggested its protector role with other virus like Hepatitis C virus. Nevertheless, in all cases, they are chronic infections or tumors, in which the cellular cytotoxic response is the only mean of the immune system to clear viral infection (Duenas-Carrera S, Alvarez-Lajonchere L, Alvarez-Obregon J C, Herrera A, Lorenzo L J, Pichardo D, Morales J. 2000. A truncated variant of the hepatitis C virus core induces a slow but potent immune response in mice following DNA immunization. Vaccine. November 22; 19(7-8):992-7; Suzich J A, Chin S J, Palmer-Hill F J, et al. 1995. Systemic immunization with papillomavirus L1 protein completely prevents the development of viral mucosal papillomas. Proc Natl Acad Sci USA; 92: 11553-57). These diseases do not correspond with the acute profile that is exhibited in the infection by Dengue in humans (Vaughn D. W., Green S., Kalayanarooj S., Innis B. L., Nimmannitya S., Suntayakorn S., Endy T. P., Raengsakulrach B., Rothman A. L., Ennis F. A. y Nisalak A. 2000. Dengue viremia titer, antibody response pattern, and virus serotype correlate with disease severity. J Infect Dis. 181: 2-9).

The capsid protein of Dengue virus has a molecular weight of 9 to 12 kDa (112-127 amino acids) and has a marked basic character because the 25% of its amino acids are arginine and lysine. The presence of these amino acids could favor antigenic presentations to the immune system due to the capacity of polycationic peptides to do so. (Lingnau K., Egyed A., Schellack C., Mattner F, Buschle M., Schmidt W. 2002. Poly-1-arginine synergizes with oligodeoxynucleotides containing CpG-motifs (CpG-ODN) for enhanced and prolonged immune responses and prevents the CpG-ODN-induced systemic release of pro-inflammatory cytokines. Vaccine. 20: 3498-3508). The protein is located totally within the virion structure without any exposed region (Kuhn R J, Zhang W, Rossmann M G, Pletnev S V, Corver J, Lenches E, Jones C T, Mukhopadhyay S, Chipman P R, Strauss E G, Baker T S, Strauss J H. 2002. Structure of dengue virus: implications for flavivirus organization, maturation, and fusion. Cell. March 8: 108(5):717-25).

Jones y cols. (Christopher T. Jones, Lixin Ma, John W. Burgner, Teresa D. Groesch, Carol B. Post, and Richard J. Kuhn. 2003. *Flavivirus* Capsid Is a Dimeric Alpha-Helical Protein. Journal of Virology, p 7143-7149, Vol. 77, No. 12) purified the capsid protein of VD2 obtained by the recombinant way in *Escherichia coli* (*E. coli*) and demonstrated that this protein behaves like a dimmer in solution without nucleic acids. Its secondary structure is mainly in form of alpha-helices and is composed by four of these helices, being one of those of greater length in the C-terminal end. The N-terminal end does not present a defined structure and its deletion does not affect the structural integrity of the protein.

This invention describes for the first time that the capsid of DEN-2 virus, obtained by a recombinant way in *E. coli* and with only a 40% of purity, is able to induce a protective immune response against the challenge with lethal DEN-2 virus in mice. It was demonstrated that this highly purified protein, retained its protective capacity, which was surpassed in the immunization of mice with the particulated form of the molecule. Moreover, it was demonstrated that the reached protection was mediated by CD8+ T-cells, a novel element considering that the reported T-cells epitopes for the capsid so far, are recognized by CD4+ T cells (Gagnon S J, Zeng W, Kurane I, Ennis F A. 1996. Identification of two epitopes on the dengue 4 virus capsid protein recognized by a serotype-specific and a panel of serotype-cross-reactive human CD4+ cytotoxic T-lymphocyte clones. J Virol. 70(1): 141-7; Simmons C P, Dong T, Chau N V, Dung N T, Chau T N, Thao le T T, Dung N T, Hien T T, Rowland-Jones S, Farrar J. 2005. Early T-cell responses to dengue virus epitopes in Vietnamese adults with secondary dengue virus infections. J Virol. 79(9): 5665-75). Additionally, this recombinant molecule was mixed with the PD5 protein, which is formed by the P64k protein of *Neisseria meningitidis* and the III domain of the envelope protein of the Dengue-2 virus. This fusion protein is able to generate a highly serotype specific, protective and neutralizing immune response, with a low probability of generating the phenomenon of antibodies dependent enhancement (Hermida L, Rodriguez R, Lazo L, Silva R, Zulueta A, Chinea G, Lopez C, Guzman M G, Guillen G. 2004. A dengue-2 Envelope fragment inserted within the structure of the P64k meningococcal protein carrier enables a functional immune response against the virus in mice. J Virol Methods. 2004 January; 115(1):41-9).

The obtaining of a genetic construction formed by the fusion of the capsid protein and the III domain of the envelope protein is also described to reach the same objective. As a result, the two formulations where the capsid is combined with the III domain of DEN-2, generated a lymphoproliferative response in mice higher than that generated by the capsid only, and in addition a serotype specific antibodies response higher than the generated by PD5 only. This last result demonstrates the immunoenhancing capacity of the capsid protein of dengue virus in the generation of Abs by a heterologous antigen, phenomenon described for other recombinant capsids from other viruses like the hepatitis B virus (Alvarez J C, Guillén G. Formulations containing virus like particles as immunoenhancers by mucosal route. Cuban office of the Industrial property. CU 1998/183).

DETAILED DESCRIPTION OF THE INVENTION

The objective of this invention is to obtain a recombinant protein corresponding to the capsid protein of Dengue virus, which generates a protective response against the infection with the lethal virus when is inoculated in mice.

The gene codifying for the capsid protein of Dengue virus was inserted into a plasmid containing the phage T5 promoter. The cells XL-1Blue, transformed with the recombinant plasmid, expressed high levels of the resulting protein.

This protein was purified approximately till a 40% of purity, and was adjuvated in aluminum hydroxide to be inoculated in Balb/c mice. A month upon the last dose the antiviral antibody response was measured. At the same time the lymphoproliferative response in spleens stimulated in vitro with the dengue virus was determined. As a result no antiviral antibodies were induced while a significant lymphoproliferative response was detected. In parallel, in not bleeding mice, the protection assay was done. A lethal doses corresponding to 100 $LD_{50}$ of Dengue virus was inoculated, the disease symptoms and death were observed during 21 days. As a result a 44% of survival-immunized mice were obtained while in the negative control group all mice died. This is the first evidence of a protective response against Dengue virus by the immunization only with the capsid protein.

Later, a high-resolution purification process was conducted, obtaining a 95% of purity of the recombinant protein.

Both preparations, the semi- and purified ones, were analyzed by HPLC to know the aggregation state of the protein in each sample. In the semipurified preparation was detected a fraction with lower retention times, while in the purified sample a retention time corresponding to the dimeric form of the molecule was detected.

To obtain an aggregation state in the purified variant, an in vitro particulation process employing low quantities of oligonucleotides was done. As a result of the process, particles of 21 nm of diameter were obtained.

The dimeric and particulated preparations, both with more than 95% of purity, were inoculated in mice. The dimeric preparation was adjuvated with Freund Adjuvant and aluminum hydroxide, while the particulated variant was adjuvated only with aluminum hydroxide.

Similar to the semipurified preparation, high levels of lymphoproliferation were detected. In the protection assay a 40 and 20% of survival were obtained with the dimeric preparation adjuvated with Freund and aluminum, respectively; however, the particulated protein adjuvated with aluminum induced a higher protection percentage.

These results together with those obtained with the semipurified protein showed the capacity of the capsid protein of inducing a protective response in Balb/c mice and demonstrated the superiority of the particulated form of the protein, letting it to be used to humans in the future together to the aluminum hydroxide as adjuvant. Additionally, not inducing an antiviral response would eliminate the phenomenon of antibodies dependent enhancement as a risk factor for the occurrence of the most severe form of the disease: the dengue hemorrhagic fever.

With the aim to determine the possible mechanism of protection, which it is not related to the induction of Abs due to its demonstrated absence, a study of CD8+ cells depletion was made. As a result, the protection reached with pure proteins of each variant was dependent of the presence of the cells that present this marker, since eliminating them the induced protective effect disappear.

Similarly, a study was made to know if the combination of the particulated recombinant capsid with antigens inducing humoral response does not affect the generation of the lymphoproliferative response and to count with a mixture of immunogens able to contribute to both branches of the immune response. To this end, the purified particulated variant of the capsid and a fusion protein containing the III domain of the envelope protein of the dengue-2 virus was inoculated in mice, which is able to generate a serotype-specific immune response diminishing the phenomenon of ADE (Hermida L, Rodriguez R, Lazo L, Silva R, Zulueta A, Chinea G, Lopez C, Guzman M G, Guillen G. 2004. A dengue-2 Envelope fragment inserted within the structure of the P64k meningococcal protein carrier enables a functional immune response against the virus in mice. J Virol Methods. 2004 January; 115(1):41-9). When administering three doses and analyzing the raised Abs, it was demonstrated a higher induction of antiviral serotype specifics Abs. As well, a lymphoproliferative response higher than that induced only by the capsid and significantly higher than that induced by the fusion protein was detected.

In parallel, to know whether it is possible to obtain the combination effect using a genetic fusion of both antigens, a plasmid containing the III domain of the envelope protein of DEN-2 virus fused to the N-terminal of the capsid protein gene was constructed. The resulting protein, with a 40% of purity, generated in Balb/c mice a lymphoproliferative response higher than that induced by the capsid alone and a serotype specific antibodies response higher than that induced by PD5.

FIGURES DESCRIPTION

FIG. 1. Cloning strategy of the capsid protein of DEN-2 virus to generate PDC-2. DEN2 C: Fragment of the capsid protein of DEN-2.

FIG. 2. Analysis by SDS-PAGE at 15% of the PDC-2 semipurification process. 1. Rupture supernatant. 2 and 3. Fraction not adsorbed to Q Sepharose FF. 4. Fraction eluted with NaCl 1M.

FIG. 3. Analysis by SDS-PAGE at 15% of the PDC-2 purification process. 1. Rupture supernatant, 2. Fraction not absorbed to the gel, 3. Washed (350 mM NaCl), 4. Eluted fraction (750 mM NaCl), 5. Fraction in Tris 10 mM, EDTA 1 mM.

FIG. 4. Chromatographic profile in Superdex 200 of the semipurified (A) and pure (B) preparations of PDC-2.

FIG. 5. Electronic microscopy pictures of the pure PDC-2 preparation before (A) and after (B) the treatment with oligonucleotides.

FIG. 6. Cloning strategy of the capsid protein of DEN-1 virus to generate PDC-1. DEN1 C: Fragment of the capsid protein of DEN-1.

FIG. 7. Analysis by SDS-PAGE at 15% of the PDC-1 semipurification process. 1. Molecular weight marker. 2. Rupture supernatant 3. Fraction not adsorbed to Q Sepharose FF.

EXAMPLES

Example 1

Cloning and Expression of PDC-2

The nucleotide sequence that codes for amino acids 1 to 99 of the capsid protein from DEN-2 virus (Sequence No. 3), was amplified with the oligonucleotides identified in the sequence list as Sequence No. 1 and Sequence No. 2 from the DEN-2 virus strain genotype Jamaica (Deubel V., Kinney R. M., Trent D. W. Nucleotide sequence and deduced amino acid sequence of the nonstructural proteins of Dengue type 2 virus, Jamaica genotype: Comparative analysis of the full-length genome. Virology 1988.165:234-244).

The vector was created by digestion of the plasmid pQE-30 with BamHI/HindIII, which contains the phage 15 promoter and a 6-histidine tail in the N-terminal region (Sequence No. 6). Upon ligation, the potential recombinants were analyzed by restriction enzyme digestion and positive clones were sequenced to check up the junctions.

Competent cells XL-1 Blue (Hanahan D. 1983. Studies on transformation of *Escherichia coli* with plasmids. J. Mol. Biol. 166:557-580) were transformed with the selected clone called pDC-2 (FIG. 1 and Sequence No. 4). The transformed *E. coli* strains were cultivated in Luria Bertani medium (LB) supplemented with Ampicilline 50 μg/mL for 10 h at 37° C. Isopropyl-B-D-thiogalactopyranoside (IPTG) to a final concentration of 1 mM was used for the induction of the promoter. Upon growing the colony, an SDS-PAGE of the cellular lysate was done. As a result, a 15-kDA band was obtained.

The protein was recognized by an anti-DEN-2 hyperimmune ascitic fluid (HMAF). This protein was denominated PDC-2 (Sequence No. 5).

Example 2

Semipurification and Characterization of PDC-2

The biomass obtained from the *E. coli* strain transformed with pDC-2 and grown at 37° C. was disrupted by French press. The recombinant protein was obtained equally distributed between the soluble and insoluble fractions. The soluble fraction was subjected to an anionic interchange chromatography, using a Q Sepharose FF column and the buffer Tris 10 mM pH 8. The protein in the non-absorbed fraction was obtained with 40% purity and was used for the immunological studies (FIG. 2).

Example 3

Immunological Evaluation of Semipurified PDC-2

Three groups of 30 Balb/c mice were used. Two of them were immunized with 10 ug of the recombinant protein by intraperitoneal route, using Freund's Adjuvant (FA) in one of the groups and aluminum hydroxide in the other. The soluble fraction resulting from the rupture of the pQE-30-transformed cells was used as negative control adjuvanted with FA; 10 animals were bled 15 days after the third dose and the antibody titers against DEN-2 were determined by ELISA. After the immunization with the recombinant protein, formulated in either adjuvant, no antibody titers were obtained.

Table 1. Antibody titers against DEN-2 from the sera obtained upon immunization of mice with semipurified PDC-2.

TABLE 1

Antibody titers against DEN-2 from the sera obtained upon immunization of mice with semipurified PDC-2.

| | ELISA Titers against DEN-2 | | |
|---|---|---|---|
| Mouse | PDC-2 Freund A. | PDC-2 Aluminum hydroxide | XL-1 Blue Freund (Neg. Control) |
| 1 | <1:100 | <1:100 | <1:100 |
| 2 | <1:100 | <1:100 | <1:100 |
| 3 | <1:100 | <1:100 | <1:100 |
| 4 | <1:100 | <1:100 | <1:100 |
| 5 | <1:100 | <1:100 | <1:100 |
| 6 | <1:100 | <1:100 | <1:100 |
| 7 | <1:100 | <1:100 | <1:100 |
| 8 | <1:100 | <1:100 | <1:100 |
| 9 | <1:100 | <1:100 | <1:100 |
| 10 | <1:100 | <1:100 | <1:100 |

Example 4

Protection Assay

For the evaluation of the protection conferred to mice against challenge with lethal homologous DEN virus by the immunization with the described variants, 10 mice were used from each of the groups immunized with the recombinant protein adsorbed in aluminum hydroxide and with the control preparation. Each animal received a dose of 100 $LD_{50}$ of lethal DEN-2 virus by intracranial inoculation and was observed for 21 days to obtain the percentages of lethality in terms of death by viral encephalitis. As a positive control, a group of 10 mice immunized with infective DEN-2 virus ($10^4$ pfu) was used. All mice in the positive control group survived, while in the negative control group all mice were sick by day 7-11 after challenge and 100% mortality was obtained by day 21. Finally, the group immunized with the recombinant protein PDC-2 presented 44.4% protection (table 2).

TABLE 2

Percentage of survival in PDC-2 immunized mice upon challenge with the homologous lethal Dengue virus.

| Immunogen | Survival percentage |
|---|---|
| XL-1 blue | 0 |
| DEN-2 | 100 |
| PDC-2 alum. | 44.4 |

* It was calculated: (# de survivors)/(total # of mice). Data of survivors were taken 21 days after challenge.

Example 5

Lymphoproliferative Response

The rest of the animals from the group immunized with the capsid protein adjuvanted with aluminum hydroxide were sacrificed 30 days after the last dose. Then, their spleens were extracted and the lymphoproliferative response to DEN-2 was studied. The results in table 3 show the stimulation indexes obtained.

TABLE 3

Stimulation indexes against the homologous serotype of the lymphocytes from immunized mice.

| | PDC-2 Aluminum hydroxide |
|---|---|
| DEN-2** | 8* |
| Control Antigen*** | 1.5 |
| PHA**** | 7 |

*Stimulation index: quotient average of counts/minutes of samples between counts/minutes of the ADN spontaneous synthesis control.
**Preparation of DEN-2 infected mice brain.
***Preparation of not infected mice brain.
****Phytohemaglutinina Mitogen (Positive Control).

Example 6

Purification of PDC-2

The biomass obtained from the *E. coli* strain transformed with pDC-2 and grown at 37° C. was disrupted by French press. The recombinant protein was obtained equally distributed between the soluble and insoluble fractions. The soluble fraction was subjected to a cationic interchange chromatography, using an SP-Sepharose FF column and the buffer Tris 10 mM, Tween 0.5%, urea 7M, pH 8. The column was washed with buffer diethanolamine 30 mM, NaCl 350 mM, pH 10.3. The elution of the protein of interest was done with buffer diethanolamine 30 mM, NaCl 750 mM, pH 10.3. Once eluted the protein, the buffer was exchanged using G-25 columns.

Finally, the protein was obtained with 96% purity in buffer Tris 10 mM, EDTA 1 mM (FIG. 3).

Example 7

Characterization of the Semipurified and Purified Variants

With the aim of characterizing the state of aggregation of the semipurified and the purified preparations, gel filtration chromatographies were done using the TSK-5000 column (Tosoh bioscience, Japan). After applying the semipurified sample, a homogeneous and major peak was obtained, with a retention time ranging from 15 to 20 minutes, evidencing the presence of high molecular weight species (FIG. 4A). Contrarily, in the sample from the highly purified fraction of the capsid protein, retention times of 30 minutes were detected, corresponding to the dimeric form of the molecule (FIG. 4B).

Example 8

Studies of Reparticulation "In Vitro"

In order to reparticulate the pure capsid protein in a dimeric form, the buffer was exchanged to Hepes 25 mM, KAc 100 mM, MgAc2 1.7 mM, pH 7.4. After heating the protein and the mixture of oligonucleotides for 1 min at 37° C., they were incubated in an equal volume for 30 min at 30° C. As a negative control of the experiment, the protein was incubated without the oligonucleotides. When both preparations were observed with an electron microscope, a large quantity of particles of approximately 21 nm diameter, were observed in the sample of protein previously incubated with the mixture of oligonucleotides, while in the control sample no particles were observed (FIG. 5).

Example 9

Immunological Evaluation in Mice of the Purified Capsid

Five groups of 20 Balb/c mice were used. Two of them were immunized with 10 ug of the dimeric purified recombinant protein by intraperitoneal route, using aluminum hydroxide and Freund's adjuvant. Another group was immunized with 10 ug of the purified and particulated capsid protein adjuvanted with aluminum hydroxide. The soluble fraction from the rupture of XL-1 blue cells transformed with the plasmid pQE-30 and subjected to the same purification steps than PDC-2 was used as negative control, adjuvanted with Freund's adjuvant. The fifth group was immunized with DEN-2 virus as positive control. One month after the last dose 10 animals from each group received a dose of 100 $LD_{50}$ of lethal DEN-2 by intracranial inoculation and were observed for 21 days to obtain the percentages of survival. All mice in the positive control group survived, while in the negative control group all mice were sick by day 7-11 after challenge and 0% mortality was obtained. Finally, from the groups immunized with the recombinant protein, the group immunized with pure dimeric PDC-2 presented a 20% protection when immunized with aluminum hydroxide and a 40% protection when Freund's adjuvant was used. Additionally, in the group that received the reparticulated pure protein adjuvanted with aluminum hydroxide. 90% of mice were protected (Table 4).

TABLE 4

Percentage of survival in mice immunized with the protein variants assayed upon challenge with the homologous lethal Dengue virus.

| Immunogen (adjuvant) | Survival percentage* |
|---|---|
| Xl-1 Blue (Freund) | 0 |
| Pure and dimeric PDC-2 (Aluminum) | 20 |
| Pure and dimeric PDC-2 (Freund) | 40 |
| Pure and reparticulated PDC-2 (Aluminum) | 90 |
| DEN-2 | 100 |

*It was calculated: (# de survivors)/(total # of mice). Data of survivors were taken 21 days after challenge.

Example 10

Lymphoproliferative Response

The rest of the animals from the groups immunized with the capsid protein (10 animals), either dimeric or reparticulated, adjuvanted with aluminum hydroxide, were sacrificed 15 days after the last dose. Then, their spleens were extracted and the lymphoproliferative response to DEN-2 was studied. The results in table 5 show the stimulation indexes obtained.

TABLE 5

Stimulation indexes against the homologous serotype of the lymphocytes from immunized mice.

| | Pure and reparticulated PDC-2 | Pure PDC-2 |
|---|---|---|
| DEN-2** | 10* | 4 |
| Antigen Control*** | 1.5 | 1.2 |
| PHA**** | 7 | 8 |

*Stimulation index: quotient average of counts/minutes of samples between counts/minutes of the ADN spontaneous synthesis control.
**Preparation of DEN-2 infected mice brain.
***Preparation of not infected mice brain.
****Phytohemaglutinina Mitogen (Positive Control).

Example 11

Immunological Evaluation of the Mixture Formed by PD5 and PDC-2

Twenty animals were inoculated with the mixture of 10 ug of the particulated pure capsid protein and 20 ug of protein PD5 (Sequence No. 23) in three doses spaced fifteen days apart. A group immunized with 10 ug of the pure capsid protein, a group immunized with 20 ug of protein PD5 mixed with the equivalent volume of PDC-2 but obtained from a negative control run, and a group immunized with protein P64k, the carrier protein present in the construction of PD5, were used as controls. In all cases, aluminum hydroxide was used as adjuvant.

Fifteen days after the last dose, the animals were bled and the sera tested for antiviral antibodies by ELISA. As shown in tables 6 and 7, the group immunized with the mixture developed serotype-specific antibodies with titers higher than those of the group immunized only with protein PD5 and, at the same time, titers in these two groups were higher than those in the group immunized with protein PDC-2, where no Abs against DEN-2 virus were detected. On the other hand, 10 additional animals were taken from each group for lymphoproliferation assays. The cells from the spleens of these animals were extracted and stimulated with the infective DEN-2 virus. As shown in table 8, in the group immunized with the mixture the stimulation indexes were higher than those in the group immunized with the capsid protein only. The lowest stimulation indexes were obtained in the group immunized with protein PD5.

TABLE 6

Antibody titers against DEN-2 virus in sera obtained after the immunization.

| | Groups inoculated with: | | | |
|---|---|---|---|---|
| Mouse | PDC-2 | PDC-2/PD5 | PD5 | P64k |
| 1 | <1:100 | <1:128000 | <1:64000 | <1:100 |
| 2 | <1:100 | <1:320000 | <1:32000 | <1:100 |
| 3 | <1:100 | <1:320000 | <1:64000 | <1:100 |
| 4 | <1:100 | <1:320000 | <1:16000 | <1:100 |
| 5 | <1:100 | <1:64000 | <1:64000 | <1:100 |
| 6 | <1:100 | <1:128000 | <1:128000 | <1:100 |
| 7 | <1:100 | <1:64000 | <1:64000 | <1:100 |
| 8 | <1:100 | <1:128000 | <1:32000 | <1:100 |
| 9 | <1:100 | <1:320000 | <1:64000 | <1:100 |
| 10 | <1:100 | <1:320000 | <1:32000 | <1:100 |

TABLE 7

Determination of the serotype-specificity of the antibodies contained in the mixtures of the sera obtained from each group.

| Viral Antigen | Groups inoculated with: | | | |
|---|---|---|---|---|
| | PDC-2 | PDC-2/PD5 | PD5 | P64k |
| DEN-1 | <1:100 | <1:200 | <1:200 | <1:100 |
| DEN-2 | <1:100 | 1:320 000 | 1:64000 | <1:100 |
| DEN-3 | <1:100 | <1:200 | <1:200 | <1:100 |
| DEN-4 | <1:100 | <1:200 | <1:200 | <1:100 |

TABLE 8

Stimulation indexes against the homologous serotype of the lymphocytes from immunized mice.

| | PDC-2 | PDC-2/PD5 | PD5 | P64k |
|---|---|---|---|---|
| DEN-2** | 9* | 11 | 2.1 | 1.1 |
| Antigen*** Control (−) | 1.3 | 1.6 | 1.5 | 1.2 |
| PHA**** | 7.5 | 7.3 | 7.9 | 8 |

*Stimulation index: quotient average of counts/minutes of samples between counts/minutes of the ADN spontaneous synthesis control.
**Preparation of DEN-2 infected mice brain.
***Preparation of not infected mice brain.
****Phytohemaglutinina Mitogen (Positive Control).

Example 12

CD8 Depletion Studies

The reparticulated and the dimeric capsid proteins were inoculated in Balb/c mice to obtain some evidence of induction of cellular immune response. A preparation obtained from cells transformed with the plasmid used to generate pDC-2, and by a purification process similar to the one used for the protein PDC-2, was employed as a negative control.

Three doses of the protein (20 ug) were administered to groups of 20 animals, using aluminum hydroxide as adjuvant. One month after the last dose, 1 mg of a rat anti-mouse CD8 mAb, able to deplete the cells of the mouse immune system containing this marker was administered to half of the animals of each group. On the next day, all the animals were challenged with 100 $LD_{50}$ (Median Lethal doses) of DEN-2 virus. They were observed for the onset of signs of disease and deaths were recorded.

In the case of the immunized non-treated groups, 20 and 80% protection was obtained in the groups immunized with the dimeric and the reparticulated capsid, respectively. Parallely, in the treated groups the percentage of protection was lower than in the non-treated groups: 0% protection for the dimeric PDC-2 and 10% protection for the reparticulated protein. In the case of the negative control group no protection was obtained in either the treated or the non-treated animals.

TABLE 9

Challenge assay with DEN-2 lethal virus in the animals immunized with variants of the recombinant capsid

| Groups | *Survival percentages in mice treated with the anti-CD8 mAb | Survival percentages in mice non treated with the anti-CD8 mAb |
|---|---|---|
| PCD12 reparticulated | 10 | 80 |
| PCD12 non-particulated | 0 | 20 |
| Control (−) | 0 | 0 |

*It was calculated: (# de survivors)/(total # of mice). Dataa of survivors were taken 21 days after challenge.

Example 13

Obtaining and Semipurification of the DEN-1 Protein

The nucleotide sequence that codes for amino acids 1 to 100 of the capsid protein of DEN-1 virus (Sequence No. 7), was amplified with the oligonucleotides identified in the sequence list as Sequence No. 8 and Sequence No. 10 from the DEN-1 viral strain. The vector was generated by digestion BamHI/HindIII of the plasmid pQE-30, which contains the phage T5 promoter and a 6 histidine tail in the N-terminal region (Sequence No. 6). Upon ligation, the recombinants were analyzed by restriction and the positives clones were sequenced to check the junctions. Competent cells XL-1 Blue (Hanahan D. 1983. Studies on transformation of *Escherichia coli* with plasmids. J. Mol. Biol. 166:557-580) were transformed with the selected clone called pDC-1 (FIG. 6 y Sequence No. 10). The *E. coli* strains transformed were cultivated in LB supplemented with Ampicilline 50 μg/mL for 10 h at 37° C. Isopropyl-B-D-thiogalactopyranoside (IPTG) to a final concentration of 1 mM was used for the induction of the promoter. Upon growing the colony, an SDS-PAGE of the cellular lysate was done. As a result a 15-kDA band was obtained. The protein was recognized by an anti-DEN-1 HMAF. This protein was denominated PDC-1 (Sequence No. 11).

Example 14

Semipurification and Characterization of PDC-1

The biomass obtained from the *E. coli* strain transformed with pDC-1 and grown at 37° C. was disrupted by French press. The recombinant protein was obtained equally distributed between the soluble and insoluble fractions. From the soluble fraction an anionic interchange chromatography was done, using a Q Sepharose FF column and the buffer Tris 10 mM pH 8. The protein in the non-absorbed fraction was obtained with 45% of purity, and was used to the immunological studies.

Example 15

Immunological Evaluation of Semipurified PDC-1

Two groups of 30 Balb/c mice were used. One of them was immunized with 10 ug of the recombinant protein by intraperitoneal route, using the aluminum hydroxide as adjuvant. The soluble fraction resulting from the rupture of the pQE-30-transformed cells adjuvanted with aluminum hydroxide was used as negative control. A part of the animals (10 mice) were bled 15 days after the third dose and the antibody titers against DEN-1 were determined by ELISA. After the immunization with the recombinant protein, no antiviral antibody titers were obtained.

TABLE 10

Antibodies titers against DEN-1 virus from sera obtained after the immunization with the semipurified PDC-1.

| | Anti- DEN-1 ELISA titers | |
|---|---|---|
| Mouse | XL-1 blue Control (−) | PDC-1 |
| 1 | <1:100 | <1:100 |
| 2 | <1:100 | <1:100 |
| 3 | <1:100 | <1:100 |
| 4 | <1:100 | <1:100 |
| 5 | <1:100 | <1:100 |
| 6 | <1:100 | <1:100 |
| 7 | <1:100 | <1:100 |
| 8 | <1:100 | <1:100 |
| 9 | <1:100 | <1:100 |
| 10 | <1:100 | <1:100 |

Example 16

Protection Assay

For the evaluation of the protection conferred to mice against challenge with lethal homologous DEN virus by the immunization with the described variants, 10 mice were used from each of the groups immunized with the recombinant protein adsorbed in aluminum hydroxide and with the control preparation. Each animal received a dose of 100 $LD_{50}$ of lethal DEN-1 by intracranial inoculation and was observed for 21 days to obtain the percentages of lethality in terms of death by viral encephalitis. As a positive control, a group of 10 mice immunized with infective DEN-1 virus ($10^4$ pfu) was used. All mice in the positive control group survived, while in the negative control group all mice were sick at day 7-11 after challenge and 100% mortality was obtained at day 21. Finally, the group immunized with the recombinant protein PDC-1 presented 50% of protection (Table 11).

TABLE 11

Percentage of survival in mice immunized with the protein variants assayed upon challenge with the homologous lethal DEN virus.

| Immunogen | Survival percentages* |
|---|---|
| XL-1 blue (Control −) | 0 |
| DEN-1 (Control +) | 100 |
| PDC-1 | 50 |

*It was calculated: (# de survivors)/(total # of mice). Data of survivors were taken 21 days after challenge.

Example 17

Lymphoproliferative Response

The rest of the animals of the group immunized with the protein PDC-1 were sacrificed 15 days after the last dose. Then, their spleens were extracted and the lymphoproliferative response to DEN-1 was studied. The results in table 12 show the stimulation indexes obtained.

TABLE 12

Stimulation indexes against the homologous serotype of the lymphocytes from immunized mice.

| | PDC-1 aluminum hydroxide |
|---|---|
| DEN1** | 8* |
| Control Antigen*** | 1.5 |
| PHA**** | 7 |

*Stimulation index: quotient average of counts/minutes of samples between counts/minutes of the ADN spontaneous synthesis control.
**Preparation of DEN-2 infected mice brain.
***Preparation of not infected mice brain.
****Phytohemaglutinina Mitogen (Positive Control).

Example 18

Cloning and Expression of PDC-2 DomIII

The nucleotide sequence that codes for amino acids 286 to 426 of the envelope protein from DEN-2 (Sequence No. 12), corresponding to the region of the domain 111 of the protein, was amplified with the oligonucleotides identified in the sequence list as Sequence No. 13 and Sequence No. 14 from the DEN-2 virus strain genotype Jamaica (Deubel V., Kinney R. M., Trent D. W. Nucleotide sequence and deduced amino acid sequence of the nonstructural proteins of Dengue type 2 virus, Jamaica genotype: Comparative analysis of the full-length genome. Virology 1988.165:234-244).

The vector was created by digestion of the plasmid pDC-2 with BamHI/BamHI, which contains the phage T5 promoter, a 6-histidine tail in the N-terminal region and the region corresponding to 100 amino acids of the capsid protein of DEN-2 virus. Upon ligation, the potential recombinants were analyzed by restriction enzyme digestion and positive clones were sequenced to check up the junctions. Finally the clone selected was named pDC-2 Dom III (Sequence No 15).

Competent cells XL-1 Blue (Hanahan D. 1983. Studies on transformation of *Escherichia coli* with plasmids. J. Mol. Biol. 166:557-580) were transformed with the selected clone called pDC-2 DomIII. The *E. coli* strains transformed were cultivated in LB supplemented with Ampicilline 50 µg/mL for 10 h at 37° C. isopropyl-B-D-thiogalactopyranoside (IPTG) to a final concentration of 1 mM was used to the induction of the promoter. Upon growing the colony, an SDS-PAGE of the cellular lysate was done. As a result, a 30-kDA band was obtained. The protein was recognized by an anti-DEN-2 HMAF. This protein was denominated PDC-2 Dom III (Sequence No. 16).

Example 19

Semipurification and Characterization of PDC-2 Dom III

The biomass obtained from the *E. coli* strain transformed with pDC-2 DomIII and grown at 37° C. was disrupted by French press. The recombinant protein was obtained equally distributed between the soluble and insoluble fractions. From the soluble fraction an anionic interchange chromatography was done, using a Q Sepharose FF column and the buffer Tris 10 mM pH 8. The protein in the non-absorbed fraction was obtained with 40% of purity, and was used to the immunological studies (FIG. 2).

Example 20

Immunological Evaluation in Mice of the Semipurified PDC-2 Dom III

Five groups of 30 Balb/c mice were used. One of the groups was immunized with 10 ug of the recombinant protein by intraperitoneal route, using aluminum hydroxide as adjuvant. The soluble fraction resulting from the rupture of the XL-1 Blue cells transformed with the plasmid pQE-30 was used as negative control, adjuvanted with aluminum hydroxide. Another two groups were included as controls. One of them was immunized with the protein PDC-2 and the other with the protein PD5 (this protein contains the domain III region of the envelope protein of DEN-2 virus). Ten animals from each group were bled 15 days after the third dose and the antibody titers against DEN-2 were determined by ELISA. As shown in Tables 13 and 14, the group immunized with PDC-2 Dom III developed high titers of serotype-specific antibodies against DEN-2, higher than those induced by the protein PD5. These results demonstrate that the genetic combination with the capsid protein enhances the antiviral immune response elicited by the domain III of the envelope protein.

TABLE 13

Antibodies titers against DEN-2 virus from sera obtained after the immunization with the Dom III-capsid protein.

| | Groups immunized with: | | | |
|---|---|---|---|---|
| Mouse | PDC-2 | PDC-2 Dom III | PD5 | P64k |
| 1 | <1:100 | <1:320000 | <1:32000 | <1:100 |
| 2 | <1:100 | <1:640000 | <1:32000 | <1:100 |
| 3 | <1:100 | <1:640000 | <1:64000 | <1:100 |
| 4 | <1:100 | <1:640000 | <1:64000 | <1:100 |
| 5 | <1:100 | <1:128000 | <1:64000 | <1:100 |
| 6 | <1:100 | <1:320000 | <1:32000 | <1:100 |

TABLE 13-continued

Antibodies titers against DEN-2 virus from sera obtained after the immunization with the Dom III-capsid protein.

| | Groups immunized with: | | | |
|---|---|---|---|---|
| Mouse | PDC-2 | PDC-2 Dom III | PD5 | P64k |
| 7 | <1:100 | <1:128000 | <1:64000 | <1:100 |
| 8 | <1:100 | <1:64000 | <1:128000 | <1:100 |
| 9 | <1:100 | <1:64000 | <1:32000 | <1:100 |
| 10 | <1:100 | <1:128000 | <1:64000 | <1:100 |

TABLE 14

Determination of the serotype-specificity of the antibodies contained in the mixtures of the sera obtained from each group.

| Viral | Groups inoculated with: | | | |
|---|---|---|---|---|
| Antigen | PDC-2 | PDC-2 Dom III | PD5 | P64k |
| DEN-1 | <1:100 | <1:200 | <1:200 | <1:100 |
| DEN-2 | <1:100 | 1:320 000 | 1:64 000 | <1:100 |
| DEN-3 | <1:100 | <1:200 | <1:200 | <1:100 |
| DEN-4 | <1:100 | <1:200 | <1:200 | <1:100 |

On the other hand, 10 additional animals were taken from each group for the lymphoproliferation assays. The cells from the spleens of these animals were extracted and stimulated with the infective DEN-2 virus. Table 15 shows that in the group immunized with the combination, the stimulation indexes were higher than those in the group immunized with the capsid protein only. The stimulation indexes in the group immunized with protein PD5 were the lowest.

TABLE 15

Stimulation indexes against the homologous serotype of the lymphocytes from immunized mice.

| | PDC-2 | PDC-2 Dom III | PD5 | P64k |
|---|---|---|---|---|
| DEN-2** | 9.5* | 11.6 | 2.2 | 1.2 |
| Antigen*** Control (−) | 1.2 | 1.1 | 1.2 | 1.6 |
| PHA**** | 7.6 | 7.4 | 7.5 | 7.9 |

*Stimulation index: quotient average of counts/minutes of samples between counts/minutes of the ADN spontaneous synthesis control.

**Preparation of DEN-2 infected mice brain.

***Preparation of not infected mice brain.

****Phytohemaglutinina Mitogen (Positive Control).

Incorporation of Sequence Listing

Incorporated herein by reference in its entirety is the Sequence Listing for the application. The Sequence Listing is disclosed on a computer-readable ASCII text file titled, “sequence_listing.txt”, created on Jul. 23, 2008. The sequence_listing.txt file is 44 kb in size.

The invention claimed is:

1. A pharmaceutical composition capable of generating an immune response against Dengue virus, comprising a capsid protein of Dengue virus type 1, a capsid protein of Dengue virus type 2, a capsid protein of Dengue virus type 3, and a capsid protein of Dengue virus type 4, wherein the capsid protein of Dengue serotype 1, the capsid protein of Dengue serotype 2, the capsid protein of Dengue serotype 3, or the capsid protein of Dengue serotype 4 is fused with a capsid protein of Dengue virus type 1, a capsid protein of Dengue virus type 2, a capsid protein of Dengue virus type 3, or a capsid protein of Dengue virus type 4.

2. The pharmaceutical composition of claim 1, wherein the capsid protein of Dengue serotype 1, the capsid protein of Dengue serotype 2, the capsid protein of Dengue serotype 3, or the capsid protein of Dengue serotype 4 is fused to an immunogenic antigen.

3. The pharmaceutical composition of claim 2, wherein the immunogenic antigen is a peptide having the amino acid sequence comprising SEQ ID NO: 19.

4. The pharmaceutical composition of claim 1, further comprising a capsid protein of Dengue virus type 1, a capsid protein of Dengue virus type 2, a capsid protein of Dengue virus type 3, and a capsid protein of Dengue virus type 4, or a combination thereof.

5. The pharmaceutical composition of claim 1, further comprising an immunogenic antigen.

6. A pharmaceutical composition capable of generating an immune response against Dengue virus, comprising a) a capsid protein of Dengue virus type 1, a capsid protein of Dengue virus type 2, a capsid protein of Dengue virus type 3, and a capsid protein of Dengue virus type 4: and
b) an immunogenic antigen
wherein the immunogenic antigen is a peptide having the amino acid sequence comprising SEQ ID NO: 22.

7. A pharmaceutical composition capable of generating an immune response against Dengue virus, comprising a capsid protein of Dengue virus type 1, a capsid protein of Dengue virus type 2, a capsid protein of Dengue virus type 3, and a capsid protein of Dengue virus type 4, wherein the capsid protein is in aggregated form or particulate form.

8. The pharmaceutical composition of claim 1, further comprising a pharmacologically acceptable vehicle and an adjuvant.

9. The pharmaceutical composition of claim 1, wherein the pharmaceutical composition is suitable for oral, intramuscular, subcutaneous, mucosal, or intravenous administration.

10. A pharmaceutical composition capable of generating an immune response against Dengue virus, comprising a capsid protein of Dengue virus type 1, a capsid protein of Dengue virus type 2, a capsid protein of Dengue virus type 3, and a capsid protein of Dengue virus type 4, wherein the capsid protein of Dengue serotype 1, the capsid protein of Dengue serotype 2, the capsid protein of Dengue serotype 3, or the capsid protein of Dengue serotype 4 is fused to a peptide having the amino acid sequence consisting of SEQ ID NO: 19.

* * * * *